United States Patent [19]

Bassett et al.

[11] 4,034,700
[45] July 12, 1977

[54] SLIDE PREPARATION STATION

[75] Inventors: William W. Bassett, Wayzata; Eugene D. Johnson, Spring Lake Park, both of Minn.

[73] Assignee: Honeywell Inc., Minneapolis, Minn.

[21] Appl. No.: 689,720

[22] Filed: May 25, 1976

[51] Int. Cl.² .......................................... B05C 11/04
[52] U.S. Cl. ..................................... 118/2; 118/7; 118/9; 118/100; 118/120; 427/8
[58] Field of Search .................. 118/2, 4, 7, 9, 100, 118/104, 120, 314, 203, 256; 23/253 R; 259/81 R; 427/2, 8; 8/3, 94.11

[56] References Cited

U.S. PATENT DOCUMENTS

| | | | |
|---|---|---|---|
| 3,163,404 | 12/1964 | Kraft et al. | 259/81 R |
| 3,352,280 | 11/1967 | Hughes et al. | 118/9 |
| 3,400,726 | 9/1968 | DuGrail | 118/7 X |
| 3,589,557 | 6/1971 | Johnson | 118/100 X |
| 3,667,896 | 6/1972 | McCormick et al. | 427/2 X |
| 3,854,440 | 12/1974 | Astle | 118/7 |
| 3,880,111 | 4/1975 | Levine et al. | 118/100 X |

FOREIGN PATENT DOCUMENTS 439,124   1/1927   Germany ........................... 118/120

Primary Examiner—Mervin Stein
Attorney, Agent, or Firm—Charles G. Mersereau

[57] ABSTRACT

An integral, automated hematology slide preparation station is disclosed which includes assemblies for sample mixing, automated smearing and staining in a single unit. A rotary mixing sub-assembly is provided which interchangeably mixes vials of several sizes and requires no clips or auxiliary holding devices for the vials to be mixed. The pushbutton operated smearing or wedging sub-assembly includes a pivotally mounted, self-leveling counterbalanced reciprocating smearing arm which cams the wedging member and which, with a precise drive control produces highly repeatable blood smears containing substantially a monolayer of blood cells. The smearing sub-assembly operates in conjunction with a manually operated slide dispenser and automatic smear dryer. The staining sub-assembly is completely automatic and includes a conveyer system consisting of three synchronized, intermittently driven, conveyer sections. An input section receives the smeared slides, holds them and passes them to a staining section where the slides are carried, smeared side up, in a substantially horizontal position. The position of each slide is automatically sensed, and stain buffer solutions are applied in measured amounts at pre-determined timed intervals to the top of each slide. The slide is then tipped at an angle as it is transferred to an outlet section, rinsed, dried and stacked automatically on edge in an output magazine. Complete integrated electrical control of the system is provided along with an alarm system which signals low solution levels or low storage capacity in the output magazine.

24 Claims, 25 Drawing Figures

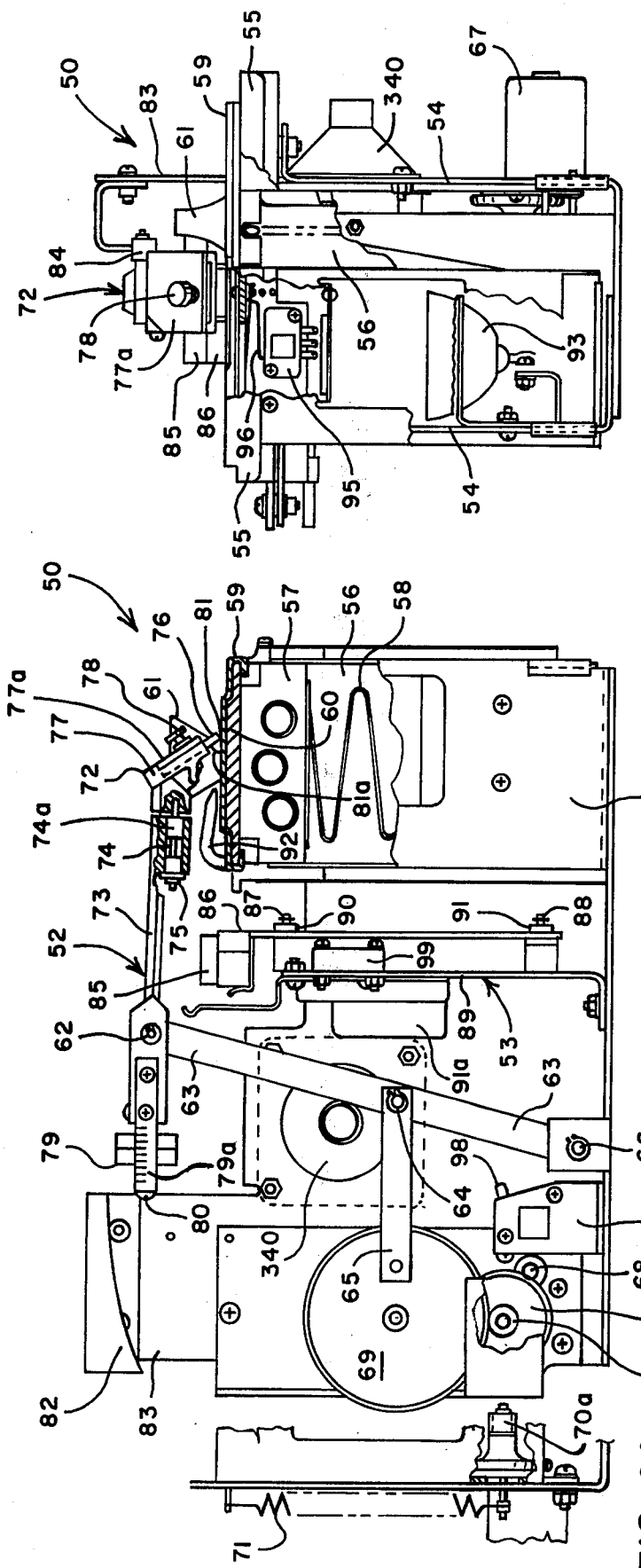

FUNCTIONAL BLOCK DIAGRAM

FUNCTIONAL WIRING DIAGRAM

| FIG. 15A | FIG. 15B |
|---|---|
| FIG. 15C | FIG. 15D |

CIRCUIT CARD DIAGRAM

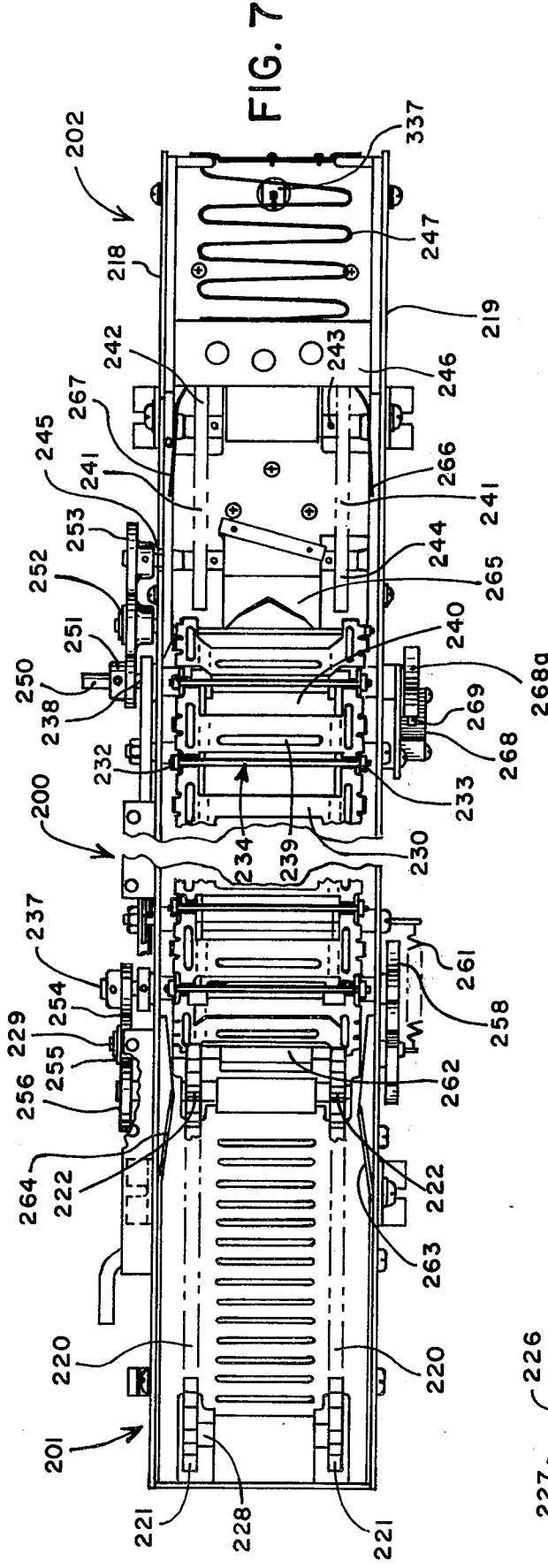
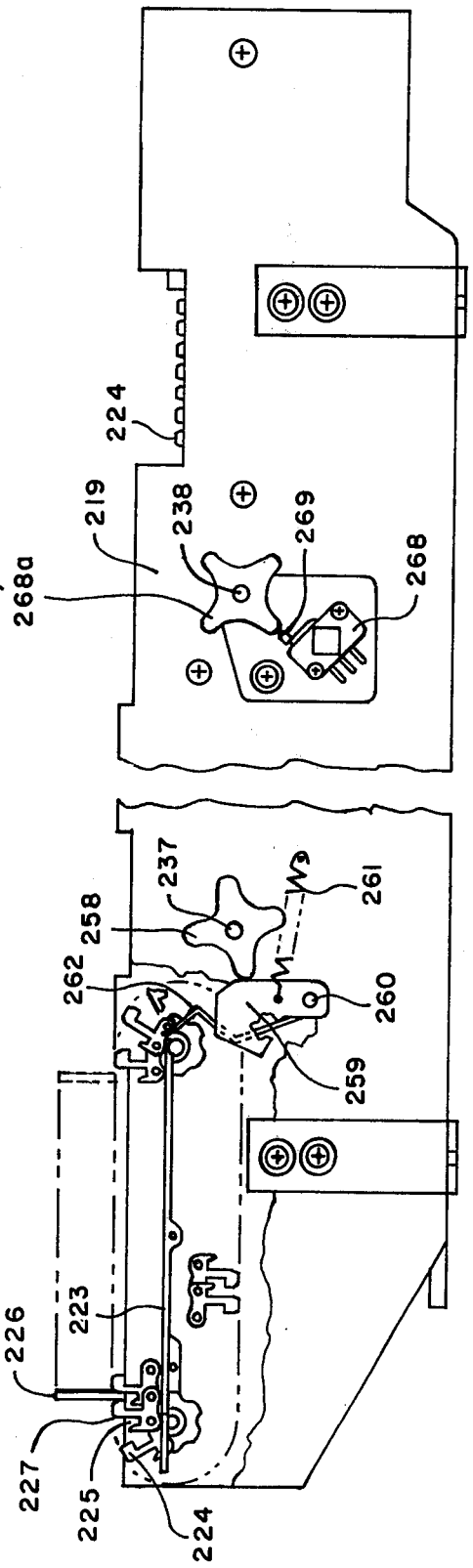
FIG. 7
FIG. 8

SLIDE PREPARATION STATION

BACKGROUND OF THE INVENTION

1. Field of the Invention

The present invention relates generally to the preparation of microscope sample slides for biological analysis and, more particularly, to an automated method of preparing smeared, stained hematology slides for microscopic analysis.

2. Description of the Prior Art

The microscopic examination of biological specimens on prepared object slides has long been an important technique in diagnostic and other medical evaluations concerning the health of patients. In this regard, the microscopic examination of smeared samples of blood is a particularly important aid to the physician.

One important example of this is the identifying and counting of the different types of white blood cells (leukocytes) found in a smear of whole blood known as a leukocyte differential count as well as other evaluations, such as red cell morphology and platelet sufficiency which require microscopic optical analysis of the blood.

Typically, when, as is generally the case, several different tests are to be run on a sample of blood, a sample of blood is drawn from a patient through a sterile needle in to a vacutainer containing an anti-coagulant and/or certain preservative or fixative agents. The sample is then transferred to the laboratory where, through a series of steps, it is prepared for the tests. The preparation of a smeared specimen slide as for a leukocyte differential count is generally as follows.

Because unmixed whole blood has a tendency to separate into layers of its constituents in order for any subsequent sample withdrawn from the specimen to be representative of the original, the original must be thoroughly mixed. Thus, the first step is normally manually attaching the vacutainer tube to a mixing device to accomplish a thorough mixing of the sample.

A small amount of the mixed sample is then withdrawn from the vacutainer, and a drop of it is placed on a microscope specimen slide. A smear of the blood is then made manually using another glass slide or other device to "wedge" the drop of blood across the slide. The smeared slide is then stained by manually applying to the smear or dipping the slide into an amount of Wrights or similar stain. This is followed by applying an amount of a buffer solution, allowing the buffer to react with the stain and rinsing the slide with a rinse solution. After the slide has been allowed to dry, it is ready for examination under a microscope.

Several attempts have been made to improve or automate various steps involved in the preparation of such blood smears for microscopic examination.

Thus, several devices have been developed in the prior art to maintain biological samples and tubular containers in a homogenized condition. One such device is disclosed in U.S. Pat. No. 3,747,900 to Dilts dated July 24, 1973. That device comprises a D.C. motor-driven, vertical plate to which clips for holding tubes or vials containing the fluid to be mixed are attached by permanent magnets or adhesive nylon strips. Another such prior art device utilizes an adjustably tiltable, motor-driven rotating disc member having a plurality of vial or test tube holding clips permanently secured thereto as disclosed in U.S. Pat. No. 3,163,404 to Kraft, et al. dated Dec. 29, 1964.

While both of these prior art devices may successfully mix fluids, they suffer from several disadvantages. Generally, the clips can accommodate tubes only of a specified diameter, and after a time the clips lose their resiliency and must be replaced. The necessity of using clips at all increases the amount of handling required which, of course, increases the likelihood of vial or tube breakage. In the case of permanently attached clips, it is quite difficult to add or remove tubes to the disc while the disc is rotating.

Several attempts have been made in the prior art to automate the creation of the smear on the blood slide. One such device is illustrated and described in a patent to Levine, et al., U.S. Pat. No. 3,880,111, issued Apr. 29, 1975, which discloses a blood smear device for automatically wedging or creating a blood smear on a specimen slide.

An example of an attempt to automate the staining of the slide is disclosed in a patent to J. B. McCormick, et al., U.S. Pat. No. 3,667,896, issued June 6, 1972.

While these prior art devices represent progress in selected areas, they all suffer certain drawbacks which detract from repeatable consistency in the preparation of stained slides for hematology. Today with the advent of automated and semi-automated devices for examining such slides, consistency in slide preparation, including such areas as the thickness and size of the smear and the coloring and highlighting of the individual blood constituents achieved by staining, is becoming critically important to the achievement of accurate, repeatable results.

SUMMARY OF THE INVENTION

By means of the present invention, many of the problems associated with the preparation of slides of stained blood smears of high quality and consistency for such things as leukocyte differential counts are eliminated by the provision of a complete automated, integrated slide preparation station. The present invention includes an improved, automated slide smearing mechanism or sub-assembly which operates in conjunction with a slide feeding mechanism and smear dryer to prepare highly repeatable substantially monolayer blood smears each from a sample of mixed blood placed on a slide. An automated slide staining sub-assembly operates in conjunction with the smearing mechanism to apply measured amounts of Wrights or other stain and buffer solutions at pre-determined intervals to the upper surface of smeared slides as they are moved substantially horizontally along on a conveying mechanism. The slides are sequentially tilted and rinsed and dried on edge automatically. The slide stainer also incorporates an input conveyer and an output storage magazine for storing the completed slides prior to microscopic examination. A mixing mechanism is also incorporated in the illustrative embodiment of the present invention which consists of a rotatable agitating member, in the shape of a disc which contains recesses to interchangeably receive containers of several sizes to be agitated. The disc is mounted at an angle to retain the containers to be agitated in a manner which eliminates the need of any clips or other artificial holding devices. A pipetting station and work area may also be provided.

BRIEF DESCRIPTION OF THE DRAWINGS

In the drawings, wherein like numerals are utilized to designate like parts throughout the same:

FIG. 4 is an enlarged, side elevational view of the smearing mechanism of the invention with parts cut away;

FIG. 4a is a partial rear elevational view taken from left to right of FIG. 4 with parts cut away;

FIG. 5 is a front elevational view of the smearing mechanism of FIG. 4;

FIG. 7 is an enlarged, broken plan view of the conveyer system portion of the staining mechanism of the present invention;

FIG. 8 is a side view of the mechanism of FIG. 7 with parts cut away;

DESCRIPTION OF THE ILLUSTRATIVE EMBODIMENT

Figure 1:
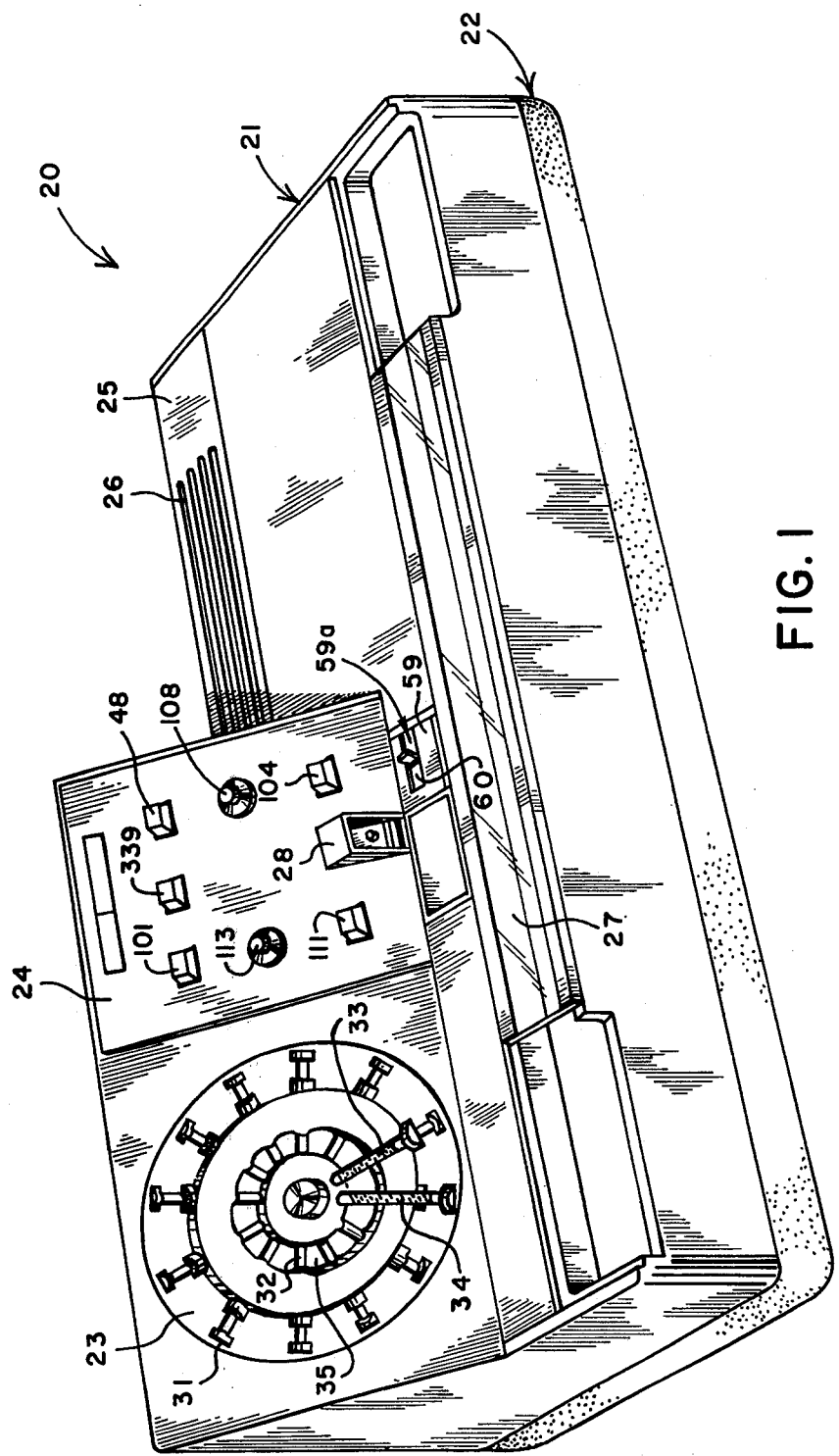
FIG. 1 is an overall, outside perspective view of an illustrative embodiment of the present invention.
Figure 2:
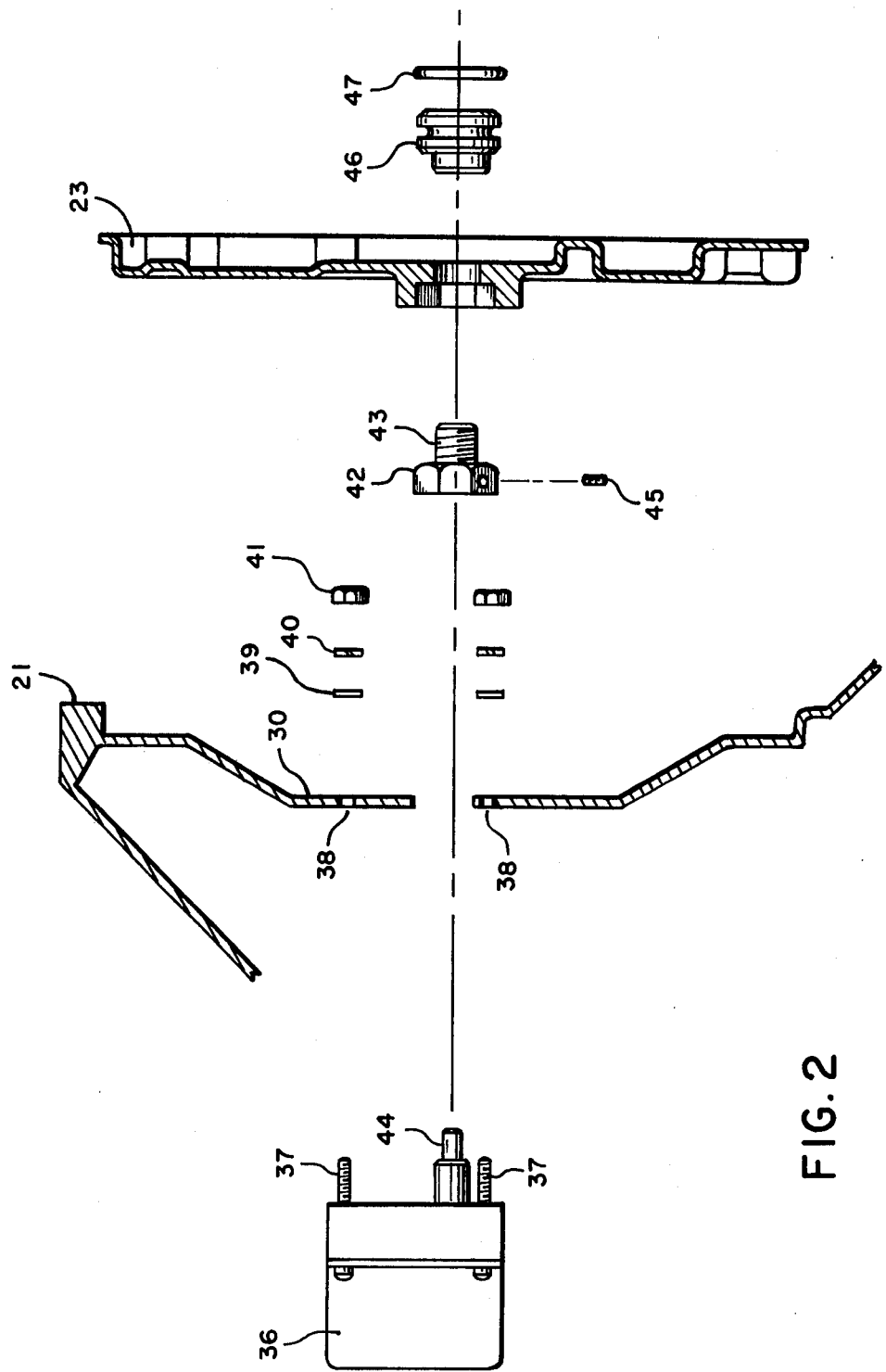
FIG. 2 is an enlarged, exploded view of the agitator of the illustrative embodiment.
Figures 6, 13, 13A, 13B, 13C, 14, 14A, 14B, 15:
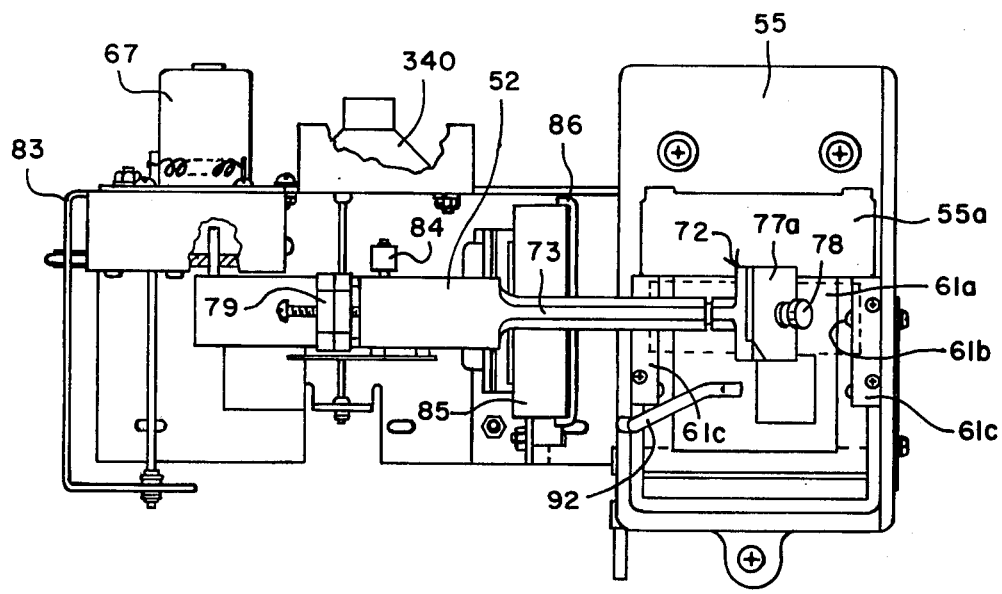
FIG. 6 is a top or plan view of the smearing mechanism of FIG. 4 with parts cut away and the slide magazine removed.
FIG. 13, including
FIGS. 13A, 13B and 13C, is a functional block diagram of the operation of the illustrative embodiment of the present invention.
FIG. 14, including
FIGS. 14A and 14B, represents a functional wiring or cabling diagram of the illustrative embodiment of the present invention.
FIG. 15, including

The entire system of the present invention includes an agitation or mixing sub-assembly which is illustrated in FIGS. 1 and 2, a slide smearing or wedging sub-assembly which is illustrated in FIGS. 3–6, a slide staining subassembly which is illustrated in FIGS. 7–12, and the integrated operation and control of the entire system is depicted by FIGS. 13–15.

It is best to begin the discussion of the illustrative embodiment by looking first at FIG. 1 which illustrates at 20 an overall outside view of a fully assembled illustrative embodiment of the present invention. As seen in that figure, the chassis of the illustrative embodiment has an upper section 21 and a lower section 22. The upper section 21 may be pivotally attached to the lower section as by rear mounted conventional hinges, the lower portion of which is shown at 22a (FIG. 3) so that it may be raised to expose the inner workings of the apparatus.

The agitation or mixing apparatus, including a mixing disc which is shown at 23, along with the control panel 24 and a pipetting station 25 which has grooves as at 26 for holding pipette tips are carried in the upper chassis section 21 along with a transparent stainer transport cover 27 and a protective hood for the smearing mechanism 28. As discussed below, the remainder of the components of the apparatus are carried or mounted in the lower chassis section 22.

MIXING SYSTEM

The agitation or mixing system of the invention is illustrated in detail by the exploded view of FIG. 2 taken in conjunction with FIG. 1. Thus, the mixing apparatus includes a supporting portion of the upper chassis structure 21 having a recessed portion 30 recessed in a manner suitable to receive the rotatable agitating disc 23. The disc 23 contains a plurality of shaped outer recesses 31 and corresponding inner recesses 32 which may be disposed radially about the disc 23. The recesses 31 are normally in the shape of the containers to be received and may be designed such that several conventional sizes of sealed containers, such as vials or test tubes, may be received interchangeably. There are respectively illustrated at 33 and 34 two conventional sizes, e.g., 5ml (12 × 75mm) or 7ml (13 × 100mm) of sealed test tubes which may be Vacutainers (trademark of Becton-Dickenson and Company of Rutherford, N.J.) or similar tubes.

The recesses 32 may have a shape similar to the recesses 31 or may be defined by intermediate raised areas as at 35. As illustrated in the perspective view of FIG. 1, the agitating disc 23 is mounted generally at an angle such that the tubes, when placed in the recesses 31 and 32, are retained there by gravity, eliminating the need for any auxiliary devices to hold them in place. While the supporting chassis structure 21 may be designed to support the agitating disc 23 at any angle which will allow the tubes to be retained in their recesses 31 and 32 by gravity, and generally any angle between 30° and 60° will suffice, mixing studies have shown that the most efficient mixing occurs at an angle of approximately 45°. Likewise, the rate of rotation is not critical. Thus, any rate which accomplishes a continual gentle agitation of the blood is acceptable. Generally, a rate between about 4 and 16 rpm is preferred. One successful embodiment rotates at a fixed speed of approximately 6 rpm.

In FIG. 2 the partial view of the supporting chassis structure 21 along with the agitation disc 23 are shown in section. A drive motor 36 is conventionally mounted on the support section 30 as by mounting screws 37 through holes 38 along with washers 39 and 40 and secured by conventional fastening means such as nuts 41. A partially threaded adapter 42 having a threaded section 43 is mounted directly on motor output shaft 44 as by a spring pin 45. An internally threaded knurled knob 46 with dampening O-ring 47 are used to secure the disc 23 to the threaded portion 43 of adapter 42.

The disc 23 may be formed with any desired shaped recesses or combination of recesses and raised areas to correspond to the particular shape of the containers in which the fluid is to be mixed. The disc may be made of any conventional, moldable plastic or other desired material, and different discs can be utilized with the same apparatus by removing the knurled knob 46 and changing same as desired.

Motor 36 illustrated in the preferred embodiment may be a conventional gear motor, such as a Series K86136 available from A. W. Haydon Company of Waterbury, Conn., which has an output speed of approximately 6 rpm. Of course, any conventional drive system, including one having adjustable or variable speeds, can be substituted for the drive illustrated in the preferred embodiment depending on the nature of the material being mixed and the size of the containers. The mixer is operated from the control console 24 as by pushbutton 48.

Thus, the conventional apparatus utilized for the mixing of containers of such fluids as blood has been greatly simplified. Short and long tubes, such as those illustrated at 33 and 34 (FIG. 1), are easily removed and replaced on the agitating disc 23 by simply grasping same in the space between the recesses 31 and 32. This can be done easily while the disc 23 is rotating.

Figure 3:
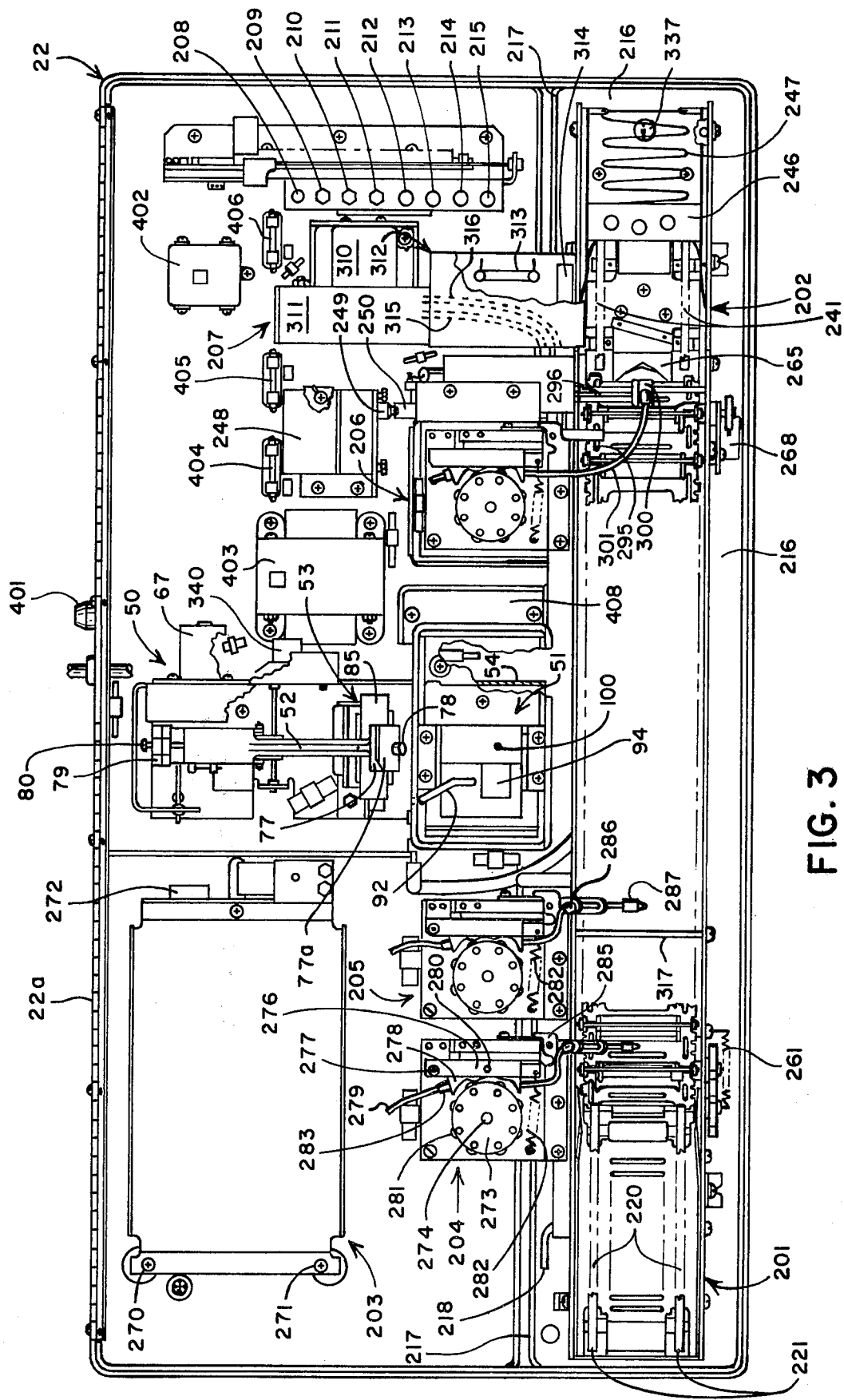
FIG. 3 is a plan view of the inside of the embodiment of FIG. 1 with certain portions cut away or items removed.

FIG. 3 illustrates a plan view of the assembly 20 with the upper chassis member 21 removed. That figure will be viewed in connection with other figures to represent and show placement of certain parts in the remaining sub-assemblies of the apparatus of the invention.

SMEARING SYSTEM

There is shown generally at 50 (FIG. 3) a plan view of this smear-making sub-assembly or wedging system of the invention, including its relation to the other sub-assemblies or systems in the illustrative embodiment. An enlarged version of that view appears in FIG. 6. A side elevation and partial rear left and front elevation views are shown in FIGS. 4, 4a and 5, respectively.

The blood smearing or wedger system prepares dried blood smears on microscope slides which are in condition for staining prior to examination. The blood wedging system basically comprises a section for feeding microscope slides to be smeared which includes a manually operated slide dispensing system located at 51, a pushbutton-operated, motor-driven wedging system having a smearing wedge mounted on a pivotally connected smearing arm 52 which is employed for making the actual blood smear automatically, cleaner system 53, and a slide dryer system for drying the smear prior to the staining of the slide.

As best seen in FIGS. 4 and 5, the slide dispensing system comprises a support structure 54, a platform member 55 adapted to receive a removable slide magazine through opening 55a. The removable slide magazine further includes a retaining member 56, generally in the shape of an open sided box, a slide pusher head 57, which with compression spring 58 retains a stack of slides (not shown) upward against a manually operated slide feed system. The manually operated slide feeder system includes a top retainer member 59 having a slot therein at 59a (FIG. 1) and a slide dispenser plate 60 which is connected to a slide dispenser knob 61 and slidably mounted in the retainer member 59, such that the pusher plate slides freely from side to side with the operation of the slide dispenser knob 61. Thus, with the smearing arm 52 retracted, a slide can be fed by moving the slide dispenser knob 61 first to the right so that a slide is pushed upward next to the slide dispenser plate 60 and then back to the left to feed a slide. This also positions the slide directly in line with the smearing arm 52 in position for a sample to be smeared. The slide shown in phantom at 61a is held in position by upward directed pressure from spring loaded members as at 61b which retain the slide ends against members 61c.

As shown in FIG. 4, the smearing arm 52 is pivotally connected as at 62 to a drive member 63 which, in turn, is pivotally connected at 64 to a bell crank drive arm member 65 and pivotally anchored to the chassis at 66. The arm 52 is driven by a motor 67 (FIG. 6) having an output shaft 68 which drives an output wheel 70 which, in turn, drives the eccentric wheel 69 at reduced speed by means of a driving hub 70a which is held against eccentric wheel 69 as by a tension spring 71.

The pivotal smearing arm 52 has a smearing head 72 which is attached to an arm member 73 as by a pin 74 with retaining ring 75. The pin 74 is journaled in hollow sleeves 74a in the arm 73 and secured to the head 72 in such a manner that the head 73 with pin 74 freely pivot within the member 73. The head 72 is symmetrically constructed such that, with the journal bearing action of the pin 74 in sleeves 74a, it will self level.

The actual smearing or wedging is accomplished by a spreading member 76 which is received between members 77 and 77a (FIG. 4) and secured therein as by a retaining thumb screw 78. The member 77 is recessed in the precise shape of the spreading member 76, and the member 77a rests on top of the assembly to retain the spreading member 76 in precise alignment.

The downward force exerted by the spreading member 76 on a slide during the smearing cycle is precisely controlled by the provision of a counter-weighted balancing system for the pivotal smearing arm 52. This includes an adjustable counterweight as at 79, and vernier scale 79a. The counterweight is threadably mounted on a stud 80 and is adjusted by rotating same on stud 80. In this manner the precise amount of counter-balance can be determined and maintained or adjusted as necessary for proper smearing. The vernier scale 79a may reflect grams of downward pressure exerted by the spreading member 76. Successful smears have been made with the application of from about 4 to about 10 grams downward pressure applied to the slide.

The smearing member 76 is provided with one or more smearing edges 81 and is normally disposed at an angle 81a of about 55° with the horizontal. Although other suitable materials may be used, the member 76 is preferably made of Quartz and may have up to four double edges so that up to eight edges are available for smearing on one such member. As one edge becomes worn, the member 76 may be rotated and/or reversed, as needed, to utilize all available edges.

A guide system is provided which causes the spreading member to raise up off the slide as it returns to the retracted position during smearing. This includes a shaped surface 82 which is carried on a bracket 83 and which cooperates with a follower member 84 to cause arm 52 to pivot as it proceeds to the left or retracts as seen in FIGS. 4 and 5.

In order that no amounts of blood be carried over from one smear to the next on the spreader member 76, a spreader or wedger cleaning assembly 53 is provided (FIGS. 4 and 6) which includes a replaceable cleaning sponge 85 carried by a vertically disposed holder member 86 which is freely slidably mounted on and pinned to cam followers 87 and 88. Cam follower 88 is attached in conventional fashion to a support member 89 as at 91. A drive motor 91a is provided which drives an eccentric wheel (not shown) to which the eccentric cam follower 87 is attached at 90 and which, when driven, cooperates in conventional fashion with substantially vertical slots in the member 86 which run vertically as member 86 is positioned in FIG. 4 (not shown) which causes the member 86 and therefore the sponge 85 to lift up, contact and sweep clean the spreader member 76 and return to a lowered position. This, of course, must be accomplished when the spreader arm 52 is in the retracted position with the member 76 located above the sponge.

A drying station is provided for drying the smeared slide prior to the staining thereof to prevent any loss or disturbance of the smear by the staining process. Drying is accomplished by a combination of air which is diverted from a blower-heating system associated with the stainer assembly (discussed in detail below in connection with the stainer sub-assembly) and supplied to the drying station of the smearing sub-assembly through an air duct 92 (FIGS. 4 and 6) and a drying lamp 93 which operates in conjunction with a uv filter drying window having an aperture 94 to provide a light of proper wave length, chiefly in the infrared end of the electromagnetic spectrum. The aperture 94 is located to correspond to the location of the thickest part of the smear which requires the most drying assistance. Use of the aperture and the filter serves also reduces the amount of glare received by the operator.

While the logic and basic wiring of the smearing sub-assembly of the invention will be discussed in detail in connection with FIGS. 14 and 15, below, the basic operating sequence of the smearing sub-assembly is discussed here.

In connection with the operation of the smearing system of the invention, three control switches are provided. A conventional microswitch 95 (FIG. 5) having a position sensitive feeler operator 96 is employed to sense the presence of a slide in position for smearing by downward vertically as member 86 is positioned in FIG. 4 (not shown) which causes the member 86 and therefore the sponge 85 to lift up, contact and sweep clean the spreader member 76 and return to a lowered position. This, of course, must be accomplished when the spreader arm 52 is in the retracted position with the member 76 located above the sponge.

A drying station is provided for drying the smeared slide prior to the staining thereof to prevent any loss or disturbance of the smear by the staining process. Drying is accomplished by a combination of air which is diverted from a blower-heating system associated with the stainer system (discussed in detail below in connection with the stainer sub-assembly) and supplied to the drying station of the smearing sub-assembly through an air duct 92 (FIGS. 4 and 6) and a drying lamp 93 which operates in conjunction with a uv filter drying window having an aperture 94 to provide a light of proper wave length, chiefly in the infrared end of the electromagnetic spectrum. The aperature 94 is located to correspond to the location of the thickest part of the smear which requires the most drying assistance. Use of the aperture and the filter also reduces the amount of glare received by the operator.

While the logic details of the smearing sub-assembly of the invention will be discussed in detail in connection with FIG. 15, below, the basic operating sequence of the smearing sub-assembly is discussed next (see also FIGS. 13 and 14).

In connection with the operation of the smearing system of the invention, three control switches are provided. A conventional micro switch 95 (FIG. 5) having a position sensitive feeler operator 96 is employed to sense the presence of a slide in position for smearing by downward positioning caused by the presence of a slide. A second micro switch 97 caused by the presence of a slide. A second micro switch 97 (FIG. 4) having an operator 98 is utilized in the operation of the smearing drive motor 67 as the operator 98 is depressed by the member 63 when it is in its extreme rearward or home position. The third micro switch 99 also has a conventional operator (not shown which is released upward by the cam follower 87 when it is in the fully down position, i.e., when the cleaning mechanism is in the down or off position.

The operating sequence of the smearing sub-assembly is shown in schematic form in FIG. 13C. Assuming as with any such device, that at the outset the master power on pushbutton 101 and the illuminate master power 102 indicate that the apparatus is operational (FIG. 13A). In normal sequence, the operation of the smearing mechanism wedger is inhibited for a time less than one second after the power is turned on. This delay allows timing circuits in the circuit card assembly (FIG. 15) to stabilize. As indicated at 103 before the operational sequence begins, the smearing mechanism or wedger arm 52 should be in the home or fully retracted position, i.e., fully to the left in FIG. 4 with the operator 98 of micro switch 97 depressed by the member 63.

Before operating the smearing system, the operator goes through a series of manual steps in preparation for the actual automatic making of the smear. These include using the manual operated, slide dispensing system 51 by operating the push knob 61 to dispense a slide into position for wedging. The operator then withdraws a sample from the appropriate vial or vacutainer by removing same from the mixer and normally removing a pipette tip from the pipetting station 25 and utilizing that to place a drop of blood in position on the slide. The apparatus may be provided with a target area as at 100 (FIG. 3) beneath the location of the slide in front of the smearing or wedging mechanism so that the drop of blood may be repeatedly placed in the correct position for smearing or wedging in relation to the slide and the device. After these steps are completed, the operator presses the operate button 104 on control panel 24 to complete the manual process preparatory to the automatic smearing or wedging as indicated at 105. The wedging mechanism, as indicated at 106, is interlocked with the micro switch 95, sure that if the operator 96 is depressed indicating the presence of a slide in position, the smearing or wedging sequence is initiated; otherwise the cycle proceeds no further. Assuming the proper conditions are met, as is indicated at 107, the wedger drive motor 67 is energized and the wedger moves under the control of a D.C. servo loop located on the circuit card assembly (discussed below in connection with FIG. 15).

Basically, however, the loop is in balance until the operate conditions are met. At that time an unbalancing D.C. voltage adjusted by an adjustable length control potentiometer which is adjusted by knob 108 on the control panel 24 is applied to this servo. The servo balances itself by supplying current proportional to the imbalance through the drive motor 67. This rapidly accelerates the motor to an operating speed proportional to the current flow. The operating speed must be constant to achieve slide to slide consistency. The current flow establishes the balance in the servo loop until the voltage through a length potentiometer or length control (below) and is shut off by a return of the member 63 to depress the operator 98 on switch 97. This is achieved after a full revolution of the eccentric wheel 69. At this point the servo is momentarily imbalanced in the opposite direction. This supplies an opposing current flow through the motor 67 and electrically breaks the motor to a sudden stop to prevent coasting past the stop position.

It should be noted in connection with the length control 108 that it adjusts the length of the blood smear made by the wedger by adjusting the speed of motor 67 and therefore that of the wedger arm 52. In the lowest position, the wedger arm 52 completes a cycle in about 2 seconds and produces an extremely short smear. In the highest position, the cycle takes about 7 seconds and produces a long smear. Good smears normally are achieved at a cycle time of about 3 to 4 seconds.

The self-leveling feature in cooperation with the counterbalance feature of the wedger arm 52 combine to achieve a repeatable, even level of pressure by the spreading member 76 on each slide to be smeared. Additionally, the rims of the wheels 69 and 70 of the drive train may be coated with a resilient material, such as rubber, as might be provided by O-ring coverings to dampen any vibrational effects that might be transmitted from the drive motor 67 through the mechanical system to the member 76 and to prevent slippage between drive parts. An embodiment utilizing rubber coated wheels has been found to present a distinct advantage over those having another type of drive system such as gears, etc. The use, in combination, of the damped mechanical system and the counterbalanced, self-leveling spreading system produces precise, repeatable results and excellent smears from slide to slide.

After actuation, the arm 52 carrying smear producing or wedging member 76 is driven to its fully extended position, such that the edge 81 of the member 76 encounters the drop of blood on the slide. The capillary action of the blood causes it to flow along the edge 81 of the member 76 and attempts to follow the spreader as it continues to move and retracts as the wheel 69 continues to rotate. As discussed above, the speed of the retracting member 76 controls and determines the rate of blood deposition which affects the length of the smear. As the smearing mechanism completes a cycle, the member 63 again depresses the operator 98 on the switch 97 which shuts off the motor 67. Thus, completing the sequence at 109 (FIG. 13C).

At this point switch 97 is in the closed position which triggers the start of the wedger cleaning motor 91a as in step 109. This also triggers the start of the infrared drying lamp timed cycle.

wedging wedgin member cleaning motor 91a drives the sponge through a motion determined by the cam and follower system on which the member 86 is mounted. Thus, the sponge is raised to the edge 81 of the retracted member 76 and then swept along the edge to remove any residue of the blood sample. This action precludes the possibility of carry over between samples and insures a clean edge for the next smear. As the cam reaches its home or original position, the switch 99 again shuts off the motor 91a.

As seen in 110, the drying lamp may be shut off by pressing the interrupt pushbutton 111 on the control panel 24 (FIG. 1) which resets the circuit card logic (discussed in conjunction with FIG. 15, below) and inhibits the drying lamp until the next wedger cycle. If this is not done, the drying timer as at 112 will time out for the predetermined period for which it is set by control knob 113 on the control panel 24 and after that, shut off. While the time can vary with relative humidity, the normal drying time for an average smear is about 30 seconds.

In the above manner the sequence is repeated for each slide to be smeared. Dried, smeared slides are transferred to the staining system where preparation is completed.

AUTOMATIC STAINING SUB-ASSEMBLY

The stainer sub-assembly is seen in plan view in FIG. 3 and details thereof are broken out in FIGS. 7–12. The main sections of the staining system, as depicted in the plan view of FIG. 3, include a slide conveyer mechanism which consists of three synchronized sections, a main or staining section 200 which is flanked by a feed or input conveyer section 201 and an output conveyer section 202; a liquid dispensing system which includes a low liquid level alarm station 203, on which the rinse container (not shown) is normally located, and stain, buffer and rinse dispensing stations 204, 205 and 206, respectively; and air delivery system 207. A control bracket 208 mounted on the chassis member 22 is also provided on which are mounted stain, buffer, and transport potentiometer adjusters 209, 210 and 211, respectively, and stain pump, buffer pump and rinse pump pushbutton operators 212, 213 and 214 along with a fast transport advance button 215. The staining conveyer section 200 is positioned in a transport tank section 216 of the lower chassis section 22 as defined by a weir 217 to prevent any leakage of the solutions used into the other portions of the chassis. A drain connection 218 is provided in the bottom of chassis member 22 which can be used to continually or periodically drain used fluids from the tank section 216.

Figure 10:
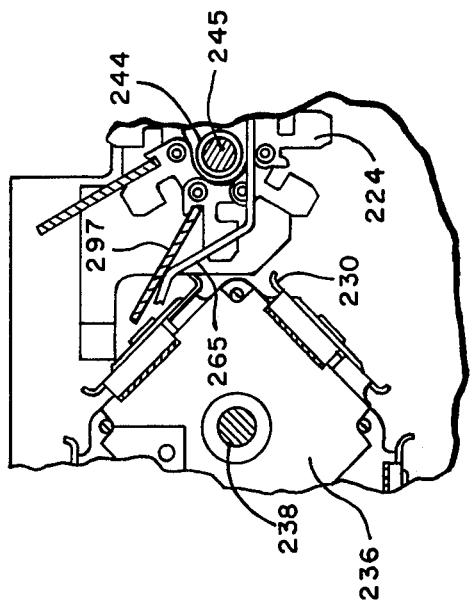
FIG. 10 is an enlarged, sectional detailed view of the output transfer portion of the conveyer system.
Figure 9:
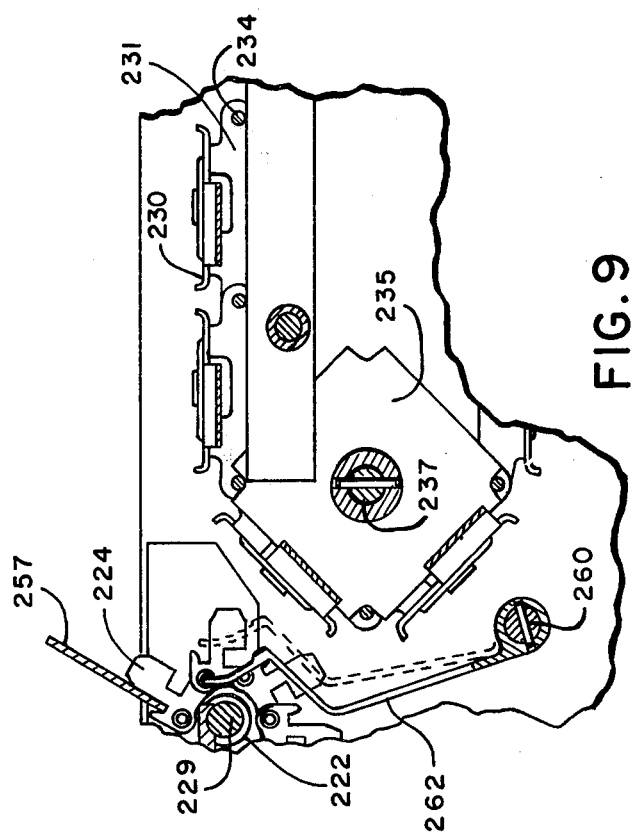
FIG. 9 is an enlarged, sectional view of the transfer detail of the entrance or feed portion of the conveyer system.

The conveyer system of the stainer is basically one which is designed to convey slides from the entry section 201 through the main conveyer where staining, buffering and rinsing are accomplished through a drying section to an exit storage conveyer without the need of any manual operation other than placing the slide on edge at the entry of conveyer section 201. An enlarged plan view, with certain parts broken away of the transport system containing sections 200, 201 and 202 is shown in FIG. 7 in the side view thereof with certain parts cut away as shown in FIG. 8. The details of the transfer mechanism from the input conveyer section to 201 to the staining conveyer section 200 and from the main conveyer 200 to the output conveyer section 202 are shown in FIGS. 9 and 10, respectively.

As shown in FIGS. 7 and 8, the entry conveyer 201 is provided with a pair of spaced endless link chains 220 which are carried on a pair of idler sprockets 221 and a pair of driven sprockets 222. The chains ride on a pair of carrier bars 223 and consist of a series of spaced riveted links 224 which have a recessed portion 225 adapted to receive the edge of a slide as at 226 and a raised portion 227 which in cooperation with the adjacent link stabilizes the position of the slide as it is carried on one side edge in a substantially vertical disposition. One end of each edge is carried by each of the chains 221. The pairs of sprockets 221 and 222 are keyed to shafts 228 and 229 to provide proper alignment of opposing links.

The staining conveyer 200 is also an endless conveyer section and is designed to convey the slide in a level horizontal disposition on segments 230. Each segment 230 is carried by a pair of spaced links 231 as can be better seen in the enlarged fractional, sectional views of FIGS. 9 and 10 which are connected as at 232 and 233 (FIG. 7) by connecting rods 234. The links 231 are carried on a pair of spaced idler sprockets 235 and spaced drive sprockets 236 which are aligned and keyed to an idler shaft 237 and driven shaft 238, respectively. The segments 230 are provided with substantial spaces between the segments as at 240 to allow adequate drainage of all fluids into the tank 216.

The output conveyer section 202 is substantially similar to the input conveyer 201. Thus, a pair of spaced endless chain 241 are carried by a pair of idler sprockets 242 keyed to a shaft 243 and driven sprockets 244 keyed to a shaft 245. The links 224 of the output conveyer are identical to those of the entry conveyer and are also designed to carry the slides on one edge in a substantially vertical disposition. The output conveyer is provided with a storage magazine having a pusher head 246 which is urged toward the left by a compression spring 247. As the number of finished slides increases, the pusher head 246 is urged to the right to provide space to store finished slides.

The three sections of the conveyer system are designed to be driven intermittently in synchronized unison by a single drive motor 248 (FIG. 3) which may be a conventional A.C. gear motor having an output shaft 249 which, in turn, is coupled to conveyer main driven shaft 249. The output conveyer section 202 is driven from the main drive shaft 250 as by gears 251, 252 and 253. Gear 253 is keyed to the drive shaft 245 of the conveyer, and the ratios of the gears 251-253 are such that when the shaft rotates sufficiently to advance segments 230 a distance equal to the width of one segment or one position, the output chains 241 will advance the width of one slide position so that the slides in the staining conveyer section 200 and the output conveyer section 201 will, in effect, index one position simultaneously.

Likewise, the entry conveyer section 201 is driven by the rotation of the main conveyer idler shaft 237 through gears 254, 255 and 256 which are also sized in such a ratio that the input conveyer will also index one position for each position moved by the conveyer 200.

As the conveyers advance in an indexing fashion, the transfer of the slides from the input conveyer 201 to the staining conveyer 200 and from the staining conveyer 200 to the output conveyer 202 is accomplished automatically. Slides carried substantially vertically on edge advance along the entry conveyer until they reach the driven sprockets 222 where as shown at 257 (FIG. 9), they begin to tilt as the opposite teeth 224 travel around the sprockets 222. Fixed to the idler shaft 237, as seen in FIGS. 7 and 8, is a star wheel cam 258. The system is so designed that the conveyer will index one position for each quarter revolution of the star wheel cam 258 in conjunction with the revolution of the shaft 237. Wheel cam 258 operates against a member 259 which is fixed on a shaft 260 and spring loaded against the cam 258 as by a tension spring 261. Also fixed to the shaft 260 so as to pivot with the rotation thereof is a slide transfer plate member 262 which is located on the shaft at a point between the endless chains 221 such that with every one-quarter revolution of rotation by the wheel 258, the slide transfer plate 262 pivots following the cam member 259 to a position shown in phantom in FIG. 9 and returns. This operation is coordinated with the advancement of the chains 221 such that the member 262 aids in transferring each slide from the input conveyer 201 to a position on one of the conveyer segments 230 of the stainer conveyer 200. Guides 263 and 264 (FIG. 7) are provided to center the slides on the conveyer both for transfer from section 201 to section 200 and also to aid in proper placement of the slide on the conveyer segments 230.

The slides are then conveyed along the conveyer section 200 until they reach the sprockets 236 at which point transfer is accomplished from conveyer 200 to the conveyer 202. The output conveyer is provided with a stationary transfer member 265 which is positioned such that as the segments 230 are tilted in going over the sprockets 236, the member 265 lifts the leading edge of each slide causing same to slide down member 265 into the respective oppositely disposed teeth 224 of the output conveyer 202 where upon they become engaged in and are carried by the output conveyer teeth 224.

The output conveyer 202 is also equipped with guides 266 and 267 to assure that the slides are properly centered on the output conveyer before they engage the pusher head 246 of the stacking magazine at the end of that conveyer.

The indexing of the entire conveyer system is accomplished by the use of a conventional micro switch 268 (FIG. 8) which has an operator 269 which is released and depressed each quarter of a revolution by a star wheel cam 268a fixed on shaft 238 and similar to cam 258. Each time the transport mechanism is called upon to advance, it advances one indexing position corresponding to one-quarter revolution by the cam 268a. The operation of a transport conveyer system is based on the implementation of a timing circuit which is discussed in greater detail below.

The liquid Dispensing System, including the staining, buffering and rinsing systems of the staining sub-assembly of the invention, is also automatic and synchronized in operation and includes conventional liquid reservoirs as plastic bottles (not shown), one each for containing solutions of stain, buffer and rinse. Because a great deal more rinse is required than of the other fluids, the rinse container is approximately 1 gallon in size, whereas the amounts of stain and buffer required to do a commensurate amount of slides may be contained in pint bottles.

The large, approximately one gallon size rinse container is carried on the fluid container holder assembly 203 which is also equipped with a low-level alarm system. Thus, the holder 203 is pivotally mounted at 270 and 271, which with the rinse bottle situated thereon, has the effect of creating a left-right pivoting fulcrum assembly. Beneath the right end of the holder assembly 203 is a micro switch 272. The micro switch 272 is operated by the weight of the holder 203 pushing against a compression spring and switch operator (not shown) in a manner which causes the switch to open when the rinse level is too low for the weight thereof to hold the spring in a sufficiently compressed position. The spring may be adjustably calibrated by a screw (not shown) such that the alarm system will signal when the desired low level amount of rinse is left in the rinse container. The stain and buffer containers should be of a size such that there will be sufficient stain and buffer for all the available rinse.

The main dispensing stations 204, 205 and 206 are located at specific intervals along the main conveyer section 200, such that time sequential administration of stain, buffer and rinse solutions may be automatically dispensed on the slide at pre-determined intervals.

The stain dispensing assembly 204 has a peristaltic pump having a rotator member 273 concentrically mounted on a shaft 274 driven by a motor 275 (FIG.

12). A channel shaped back up member 276 is pivotally mounted at 277 and contains a pivotally mounted internal back up shoe 278 which itself is shaped to contain a flexible dispensing tube 279. The member 278 is pivotally mounted within the member 276 at 280 and directs the flexible tubing 279 along a basically arcuate concave path about the rotor 273 such that as the rotor 273 rotates, freely rotatable, radially mounted wheels 281 contact the tubing 279 to cause a peristaltic pumping of the fluid within the tube 279. The combination of the pivotally mounted back up plate 276 with internally pivotally mounted member 278 in combination with a retaining tension spring 282 acts to stabilize and keep constant the pressure of the wheels 281 against the tubing 279 about the periphery of contact therewith. The tubing 279 is provided with an enlarged portion 283 to prevent slippage of the tube 279 with rotary pumping action of the pump as it rotates in a clockwise direction to pump fluid through the tube.

Figure 12:
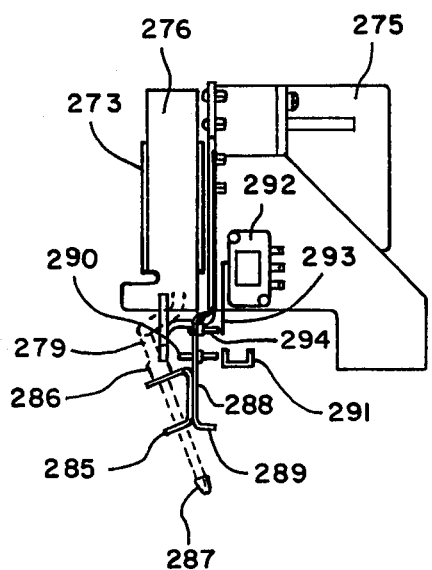
FIG. 12 is an enlarged, side elevational view of a pump and slide sensing system mechanism of the staining mechanism.
Figure 13A:
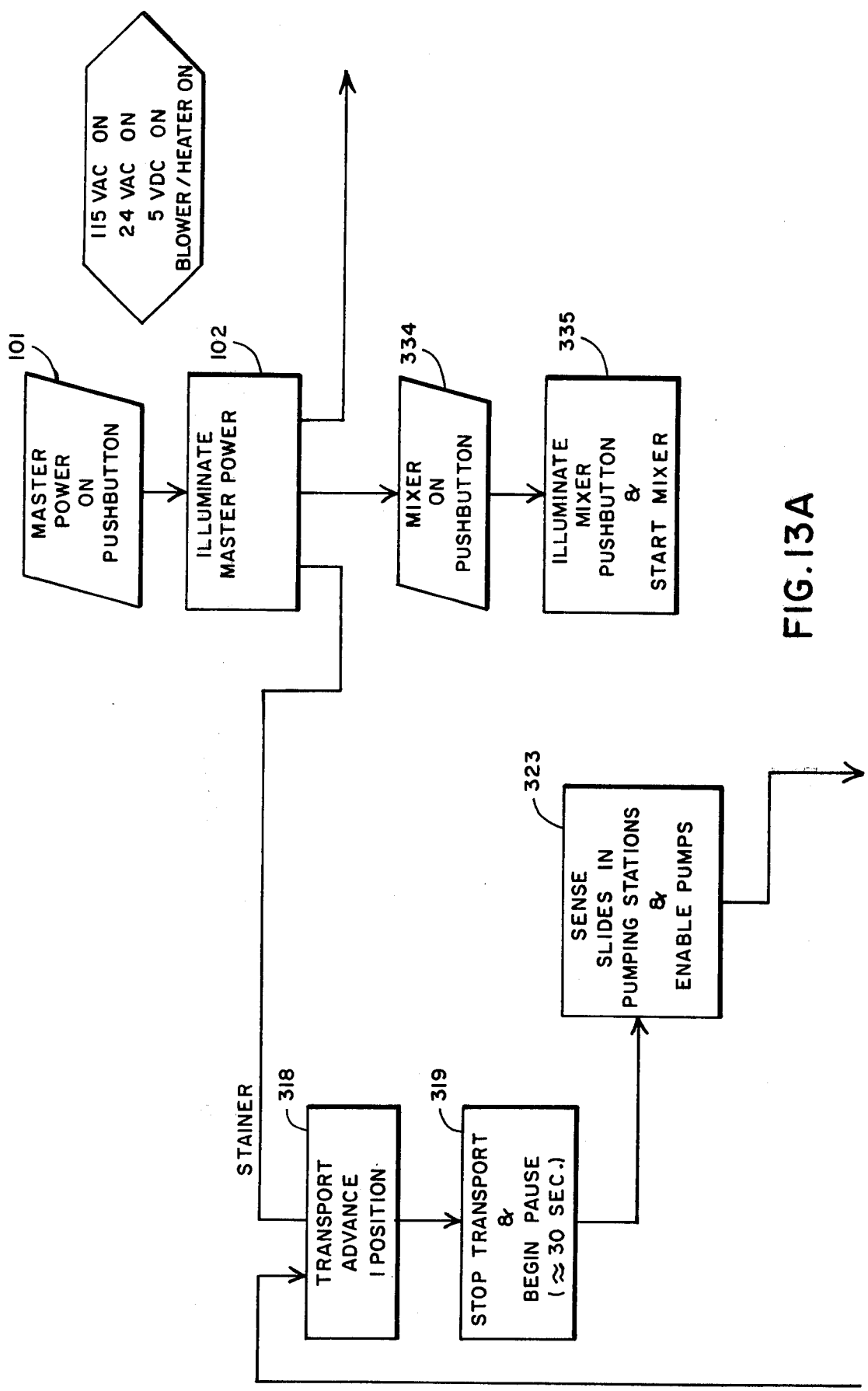
Figure 13B:
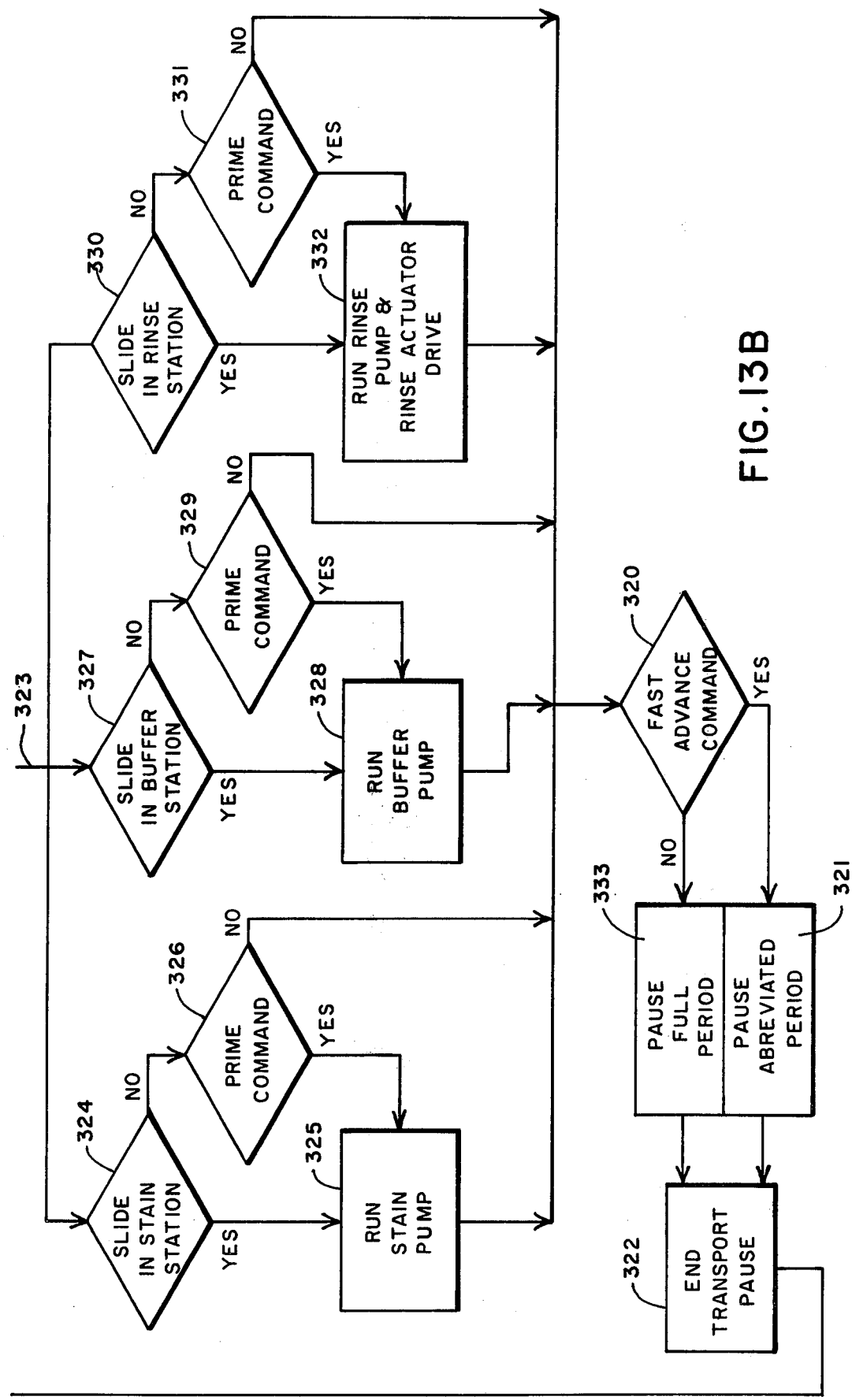
Figure 13C:
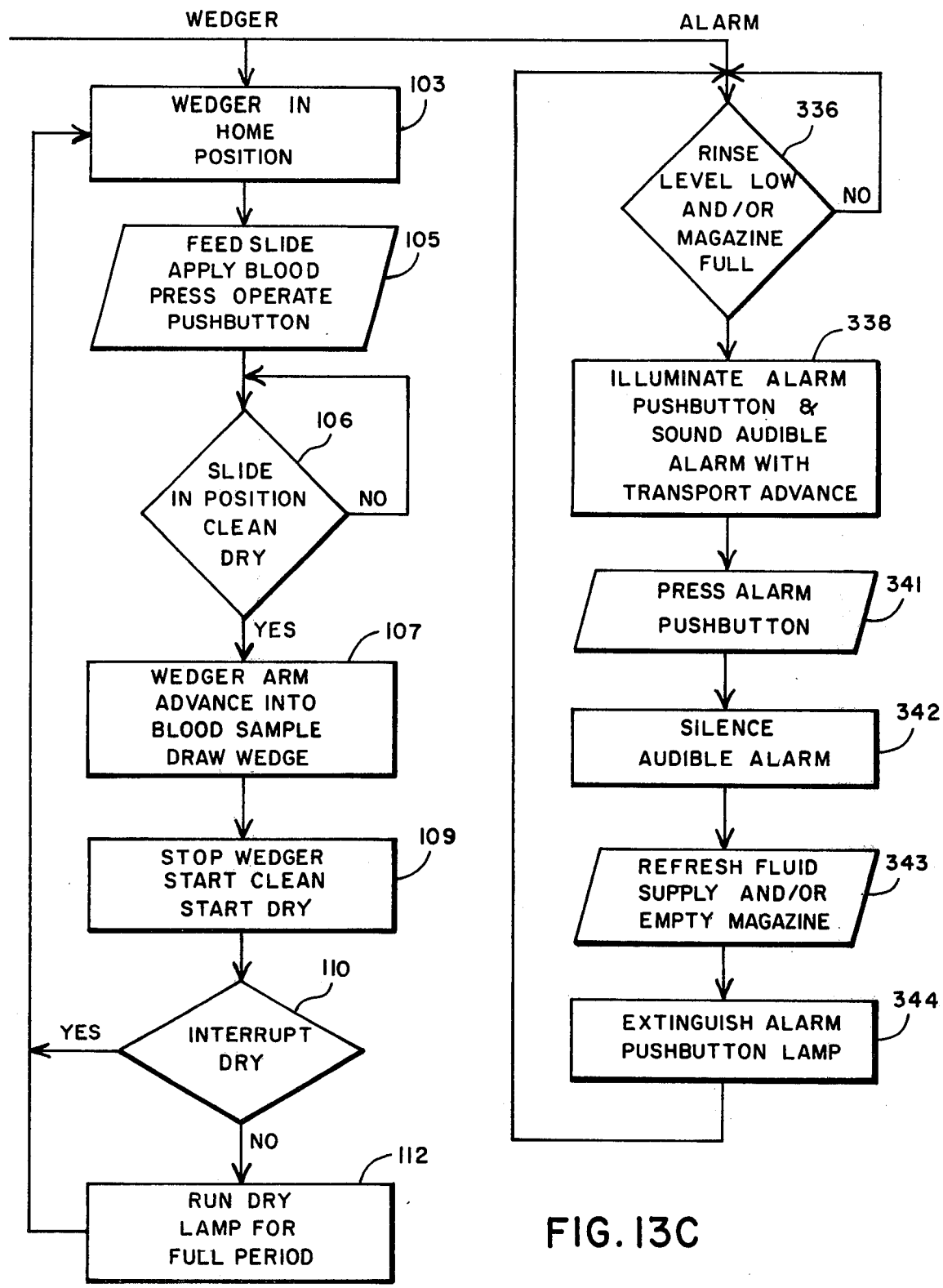
Figure 14A:
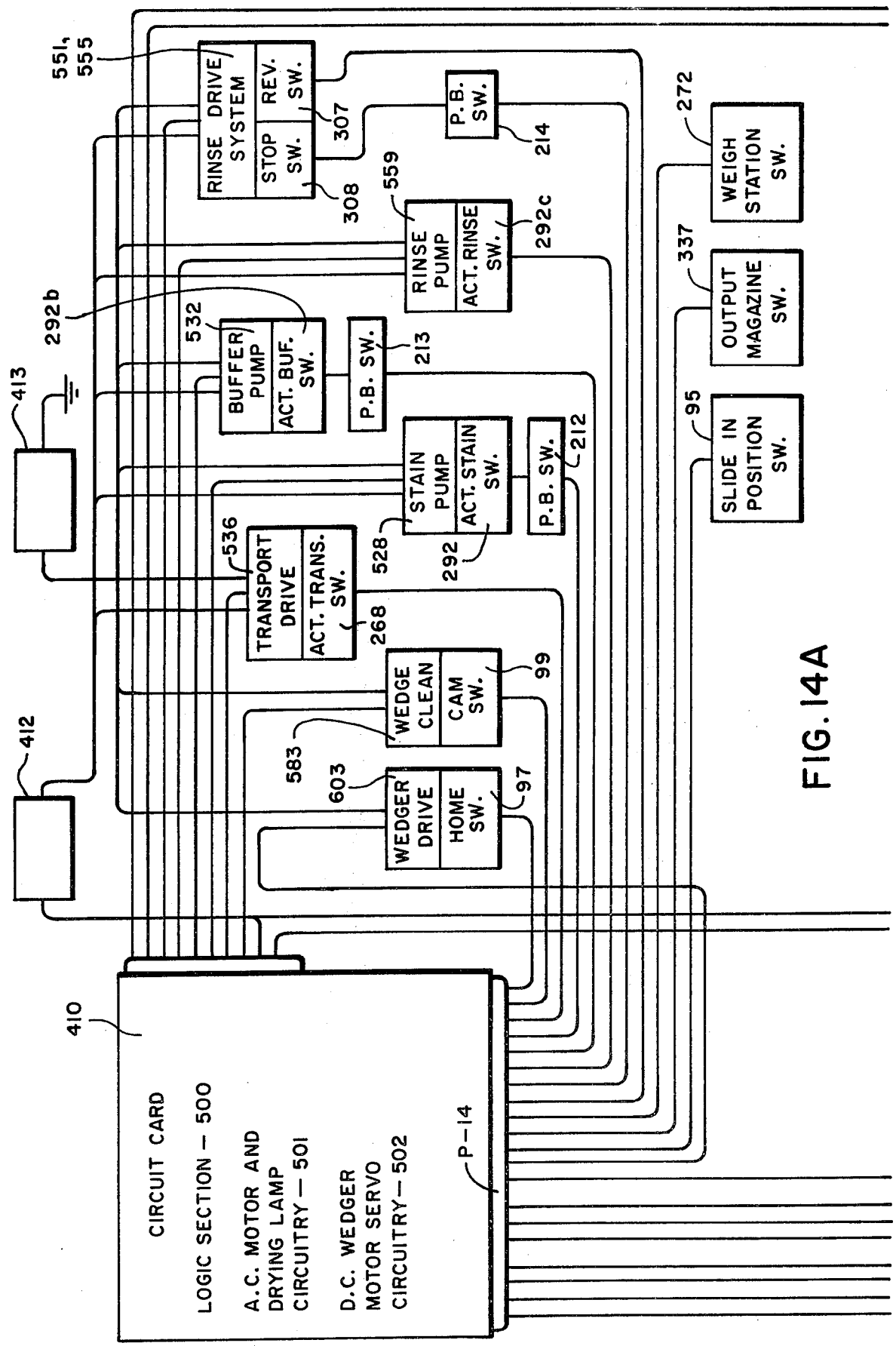
Figure 14B:
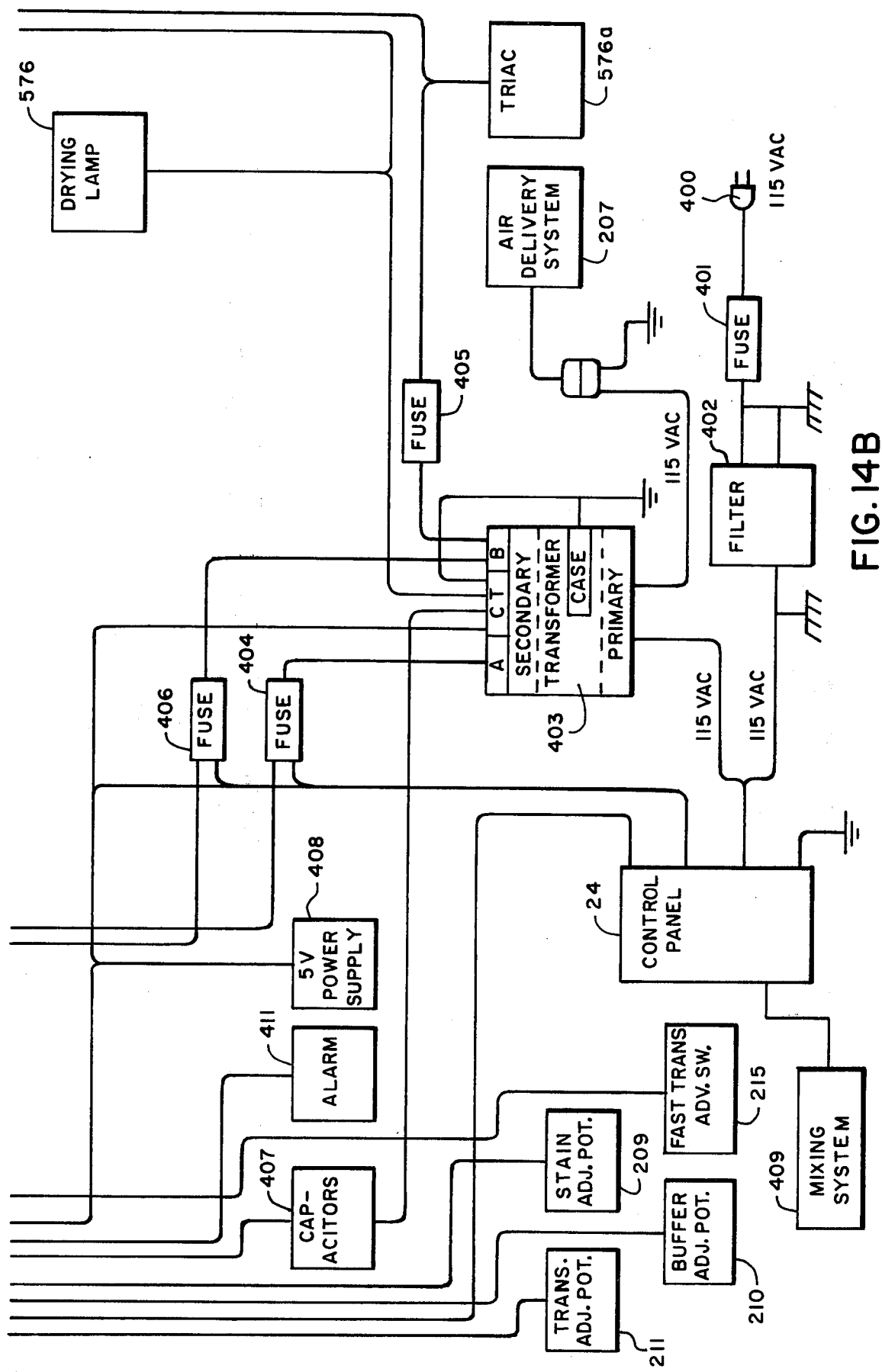

As can better be seen in FIG. 12, the tubing 279 after encountering the peristaltic pump proceeds to a mounting bracket 285 where it is retained by an additional enlarged section 286. The tube 279 terminates in a nozzle 287 from which the fluid is dispensed onto a slide. The bracket member 285 is attached to a substantially horizontally, disposed vertically pivoting member 288 having a feeler tip 289 and an adjustable lifting screw 290 which operates against a lifting rail 291 which, in turn, is alternately lifted by and lowered by conventional cams (not shown) which operate to left and lower the rail each time the transport drive indexes. Thus, the member 288 is alternately lifted and lowered with each indexing of the conveyer. An additional micro switch 292 having a fulcrum operator 293 which is contacted by an adjustable screw 294 operates in conjunction with the position of the tip 289 to sense the presence of a slide beneath the nozzle 287, as discussed below.

The buffer liquid dispensing station 205 is substantially identical to the liquid dispensing station 204 discussed in detail above and, therefore, that description need not be repeated. Likewise, the rinse liquid dispensing station 206 is generally identical to the stain dispensing station 204 but with certain minor variations which should be discussed. The slide sensing mechanism of the rinse liquid dispensing station 206 shown in FIG. 3 at 295 is located one index position before the rinse dispensing station shown generally at 296. This is because the slide must be sensed while horizontal and, when rinsed, is in a tilted position basically similar to that shown at 297 (FIG. 10) in order for efficiency and rinsing to be increased by the better drainage provided by a tilted slide. The other major difference is in the construction and operation of the rinsing mechanism itself.

Figure 11:
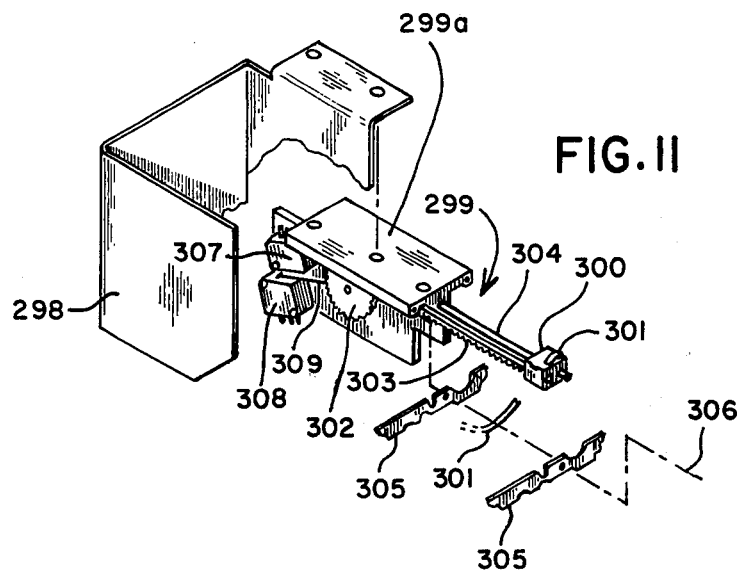
FIG. 11 is an enlarged, partially exploded, perspective view of the rinse traverse system of the staining mechanism with parts cut away.

This is best shown by the enlarged partially exploded view of FIG. 11 which depicts a rinse shield 298 and rinsing mechanism 299, mounted as by mounting plate 299a. The assembly includes a traversing nozzle 300 supplied fluid by a flexible tubing 301. The nozzle is driven by a pinion gear 302 which engages a rack 303 in conjunction with a guide rod member 304. The relative position of the sides of typical conveyer segments 230 are shown at 305 as is the center line 306 to indicate the position of the conveyer in relationship to the exploded view of FIG. 11.

A conventional A.C. drive motor (not shown) is mounted on the back side of the member 299a and adapted to drive the pinion gear 302 in accordance with control switches 307 and 308. The pinion gear drive 302 has two rod cam members attached to the gear side thereof (not shown) which, as the pinion gear 302 rotates, engage the dual switch operator level 309.

Briefly, when the rinse drive motor is actuated, it drives the rinse nozzle head 300 from right to left and, at the fully retracted position of the nozzle cam depresses the switch operator 309 downward activating the reversing switch 307 which, in turn, causes a logic circuit (discussed below) to switch the power applied to the rinse drive motor to a different motor winding, thus reversing the direction of the motor. The nozzle head then reverses the direction and, when it reaches the fully extended position as shown in FIG. 11, a second rod cam raises the operator lever 309 to activate the stop switch 308 which shuts off the rinse drive motor and the rinse pump simultaneously.

The dryer or air delivery system associated with the stainer, shown in FIG. 3 at 207, is basically a simple system which includes a conventional A.C. motor 310 which is direct coupled to a conventional blower 311, which may be a squirrel cage blower. The blower directs air into a duct 312 which contains a conventional electric heater 313. A pivotally mounted, downward directing louver is shown in part at 314 directs the air exiting from the duct 312 downward onto the output slide conveyer 202 to dry the slides as they are indexed along below the dryer duct 312. One successful model has used a blower system having a capacity of approximately 35 cfm inches (0.2 inch W.C.) and a ceramic heater which raises the air temperature about 35° F before it exits the exit duct 312.

In addition to supplying the drying air for the slides on the output or exit conveyer section 202, the dryer system 207 provides unheated air through flexible tubing 315 to the drying tube 92 of the wedger drying assembly. Also, there is provided an additional air supply through a tube 316 to a header 317 located at the slide position where the buffer is dispensed onto the slide.

The mixing manifold or header 317 has a series of spaced holes on its underside which direct air downward toward the slide in a manner which causes swirling and mixing of the stain and buffer on the slide. This added mixing feature enhances the results of staining by producing a uniform mixture of stain and buffer on the slide. This is found to be far superior to any natural mixing or mixing achieved by the angle of the applicator nozzle alone.

BASIC OPERATION OF THE STAINER SUB-ASSEMBLY

The basic operation of the stainer sub-assembly is set forth in the schematic diagram FIG. 13 and, in particular, segments 13A and 13B thereof. As with the operation of the smearing or wedging sub-assembly, with the master power on pushbutton 101 in the on position and the illuminate master power 102 indicating the apparatus is operational, the stainer mechanism is inhibited for a time less than one second to allow timing circuits in the circuit card assembly to stabilize.

The input conveyer section 201 is loaded by manually placing smeared slides vertically in the teeth 224 sequentially as they are removed from the smearing or wedging mechanism drying station. After the initial start up delay, the drive motor 248 starts driving the three synchronized units of the stainer slide conveyer and continues until the switch 268 (FIG. 8) is engaged by the cam or star wheel 268a as shown at 318.

At this point the transport motor is shut off for a period determined by a timing circuit located on the circuit card assembly (discussed below). The inactive period can be adjusted by adjusting the transport potentiometer at 211 on the control bracket 208 (FIG. 3). The inactive or pause period is shown as approximately 30 seconds at 319 in FIG. 13A, but this may be adjusted depending on the speed of the stainer assembly desired.

The pause or inactive period is required to allow for the delivery of reagents or rinse to slides in position for such delivery, allow for the mixing, staining reaction and drying to take place. The 30-second pause represents a normal average setting in which the full cycle of the conveyer drive is approximately 32.5 seconds of which 2.5 seconds is used by the movement of the transport conveyer itself.

The fast advance command 320 associated with the fast advance pushbutton 215 on the control bracket 208 greatly abbreviates and almost eliminates the pause period at 321 and 322 and enables the transport to advance another position. Thus, with the fast advance pushbutton depressed, the conveyer drive motor operates almost continually for as long as the pushbutton is held down.

After the stainer conveyer and, of course, the input and output conveyers as well, have advanced one position in normal sequence, it should be noted that the beam member 291 has been lifted by the cams, thus holding up the staining station slide sensor arm member 288 (see FIG. 12) along with the identical sensors provided for the buffering station 205 and the rinse station 206 so that they will not contact or be damaged by slides moving thereunder, and is then lowered to replace them during the final portion of the conveyer moving cycle such that any slide located in such a position would have already passed beneath the sensor. As indicated at 323, each of the slide sensors, in conjunction with its associated operator and micro switch, sense whether a slide is in the proper position for the next operation. The next, as 323 indicates, is to enable the corresponding pumps to operate in the sequence.

For example, as indicated at 324, if the slide sensing tip 289 is unable to drop to the fully downward position indicating the presence of a slide therebeneath, the switch operator 293 will not close the micro switch 292 indicating that a slide is in the stain station. As indicated at 325, this enables the stain pump to run and stain the slide which is in that position. If the sense arm 288 drops to the fully lowered position and depresses the micro switch, this indicates that no slide is in position for staining, and the stain pump is inhibited for that cycle. The prime command indicated by block 326 is associated with a stain pump pushbutton 212 which operates as an override switch which may be used to initiate pump operation as necessary for priming and/or calibration. As the priming pushbutton is pressed, it starts one cycle of its associated pump. If the pushbutton is held to the completion of the cycle, a second cycle is started at the release of the pushbutton. The action of these pushbuttons, i.e., 212, 213 and 214, is inhibited by the logic circuitry during the period of conveyer advance.

The slide in buffer station sensor and associated micro switch as indicated at 327 also operates in the same fashion as those for 328 and 329. An override pushbutton 213 is also provided. As indicated at 330, the sensing mechanism for the slide in rinse station and also the prime command override button 331 for the rinsing sequence are the same as for the stain and buffer. However, as noted above, the position of the slide is sensed one index stop before the actual rinsing takes place, therefore, the rinse pump cycle will not be initiated until the conveyer has advanced an additional position. Also, the rinse cycle as described above also contains the rinse actuator drive which runs the rinse nozzle back and forth across the tilted slide in addition to running the pump as shown at 332. As indicated at 333, if the fast advance command 320 is not initiated, the transport advance pauses for the full period to allow the various pumps and actuator drive to operate or not, as determined by the position of the corresponding slide sensor as indicated at 323.

Insofar as the stain and buffer pumps are concerned, the duration of the pumping cycle (and thus the quantity of reagent dispensed) is determined by separate timing circuits on the circuit card assembly which are discussed below. These circuits, and thus the associated pumping time, may be adjusted by tweaking their respective potentiometers 209 and 210 located on the control bracket 208.

The duration of the rinse pumping cycle is fixed by the speed of the rinse system drive. Both the rinse pump and the rinse drive motor are started at the same time. The rinse drive motor drives the rinse nozzle across the slide transport tank. At the nozzle's full retraction, as discussed above, the cam engages the reverse switch 307 on the rinse drive assembly (FIG. 11). The reverse switch signal causes a logic circuit to switch the power applied to the rinse drive motor to a different motor winding to reverse the direction of the motor. As the nozzle reaches the fully extended position, the second cam engages the stop switch 308 and the stop switch, through the signal circuit card assembly, shuts off both the rinse pump and the drive motor.

In addition to the systems already discussed, as FIG. 13A indicates, the mixer system operation sequence simply consists of a mixer on pushbutton indicated by the block at 334 which causes a light to illuminate the pushbutton 48 and start the mixer at 335. The mixer then continues to run until the on pushbutton is again depressed to turn the system off.

The final system as shown in block form on FIG. 13C is an alarm system which operates when one of two conditions exist. These conditions are, as indicated by block 336, if the position of micro switch 272 (FIG. 3) is such that it indicates the rinse level is low and/or the output magazine full switch 337 is actuated by the output magazine retainer head 246 which indicates that the output magazine has reached its capacity of slides. If either or both conditions exist, as indicated at 338, an alarm indicator and pushbutton (as shown at 339 on FIG. 1) is illuminated and an audible alarm is sounded through a speaker 340 attached to the smearing mechanism sub-assembly as shown in FIGS. 4 and 6 is energized with the next transport or conveyer advance sequence. This result is produced through logic circuits and an oscillator located on the circuit card assembly (discussed below). As shown at 341, the operator can press the alarm pushbutton 339 and silence the audible alarm at 342 if the he, she and/or it decides to continue operation. The alarm light remains on until the rinse fluid container is refilled or replaced (at 343) and/or the exit magazine is emptied to a point where both switches are no longer in the alarm position. This then, as seen at 344, extinguishes the alarm pushbutton lamp.

As discussed above, an adjusting screw is provided to vary the amount of weight required to operate the alarm switch associated with the rinse container. Normal operation indicates that the point of the alarm of the weighing station should be set to trigger at a level of rinse solution sufficient to process approximately 50 slides. This is done so that any slide which has already been placed on the inlet conveyer of the stainer system may be completely processed before the remaining stain is depleted in case there is no further supply of stain, buffer or rinse on hand.

A basic power distribution or functional wiring diagram is shown in FIG. 14 which includes FIGS. 14A and 14B. These drawings, of course, may be taken in conjunction with certain of the operations described above and in conjunction with the description of the operation of the circuit card described below.

The power distribution consists basically of an input plug 400, mainline fuse 401, a mainline filter 402 which is connected across a line to eliminate any transient peaks which might false trigger the logic circuits, a transformer 403, three fuses 404, 405 and 406 through which 24 volt A.C. lines are made available to the system, capacitors, 407 and a 5 volt D.C. power supply module 408. The power pushbutton 101 (FIG. 1) controls the line input through transformer 403 and the air delivery system 207 which is taken off the primary side of the transformer. Fuse 404 protects the line serving the mixing motor system 409 and the 5 volt D.C. power supply module 408. Fuse 405 protects the drying lamp circuit and fuse 406 protects the remaining drive motor circuits. The 5 volt power D.C. supply, of course, provides power for the logic circuits on the circuit card assembly 410. The alarm system discussed both above and below in regard to the operation of the circuit card 410 is indicated at 411. 412 and 413 denote conventional connecting terminal boards in the wiring system of the invention.

Numbers corresponding to those used in the other portions of the specification are repeated in this basic functional wiring diagram. It is believed that the diagram itself is essentially self-explanatory in view of the descriptions previously made and those pertaining to the details of the circuit card which are described next.

The next section is concerned with a description of the basic control circuitry of the invention as contained on the circuit card. The circuit card 409, as indicated in FIG. 14A, can be separated into three subsections, i.e., the logic section 500, the A.C. motor and drying lamp drive circuitry 501, and the D.C. wedger motor servo circuitry 502.

LOGIC SECTION
TURN ON DELAY CIRCUITRY

Figure 15A:
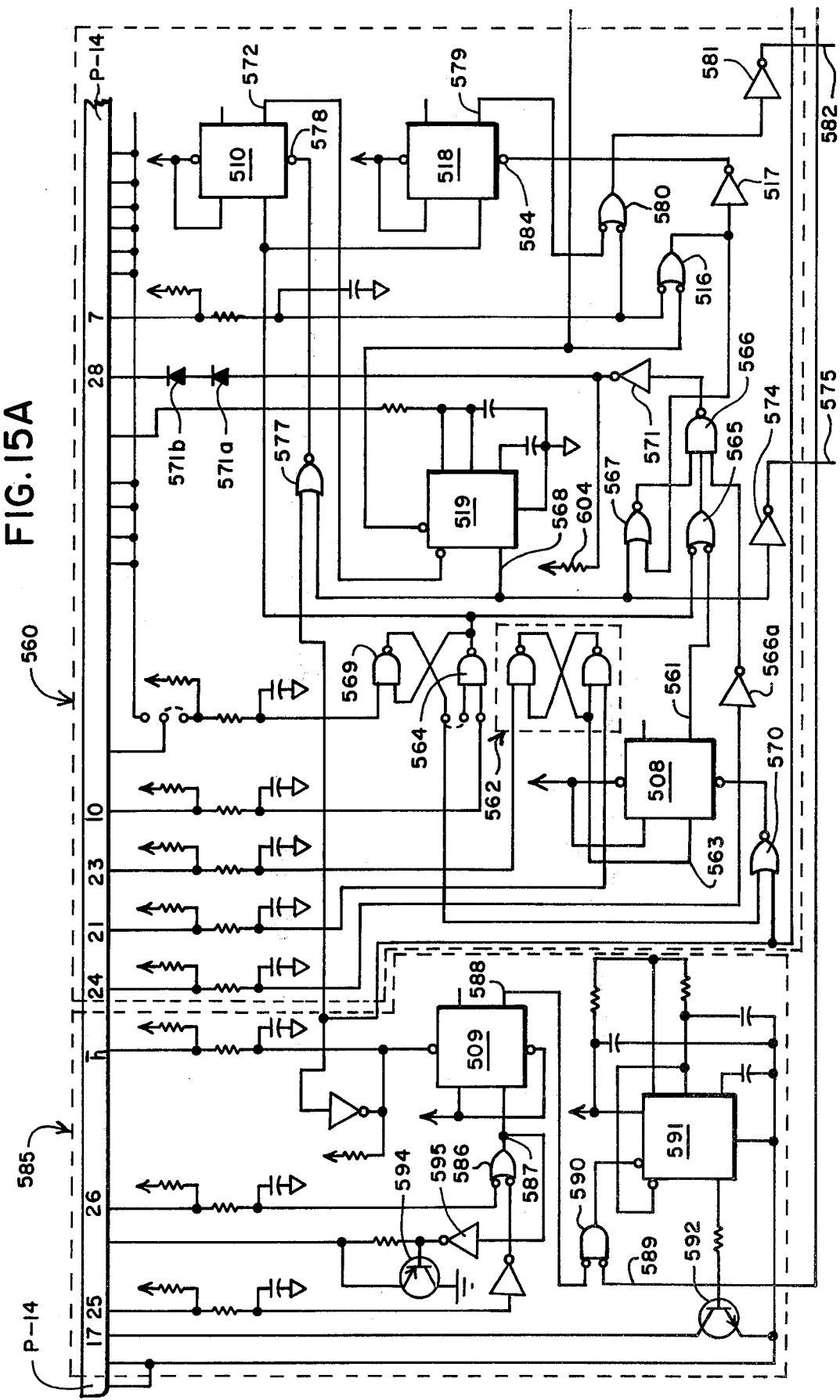
FIGS. 15A, 15B, 15C and 15D, is a schematic diagram of the circuit card of FIG. 14A.
Figure 15B:
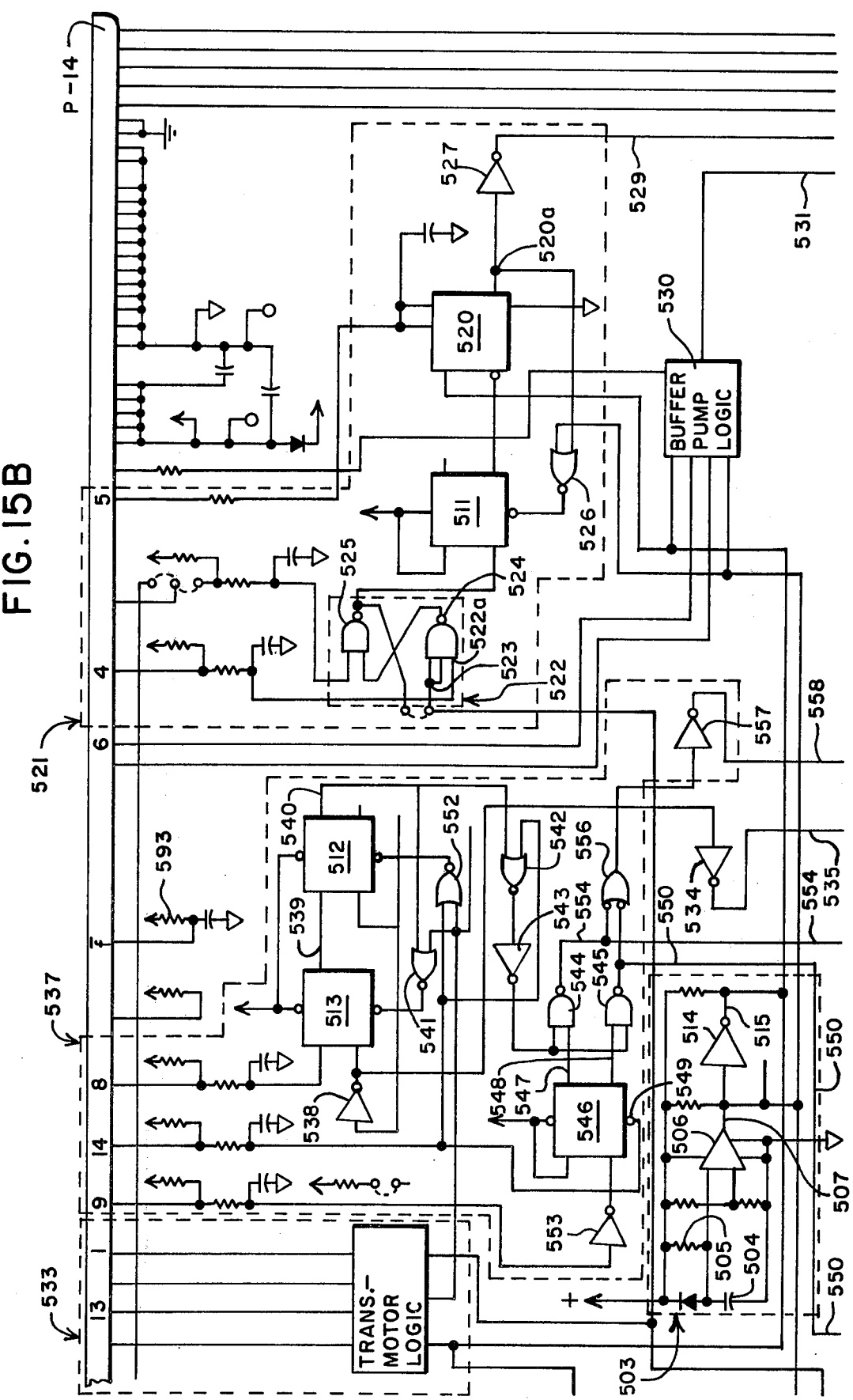

The turn-on delay circuitry is shown by the outline at 503 (FIG. 15B). Upon application of power Capacitor 504 starts charging to plus 5 volts through resistor 505. Approximately one-half second later a comparator 506 changes state and its output goes to a logic "0". During the first one-half second the logic "1" output 507 of 506 clears a number of latches or flip-flops including the following, in each case thru a nor-gate or inverting buffer: 508, 509, 510, 511, 512 and 513. The logic 1 output of 506 is sent to inverter 514, the low output 515 of which is sent to or gate 516 whose high output is sent to inverter 517, the low output of which clears latch 518. The low output 515 of inverter 514 is sent to timers including 519 and 520 and resets these timers. The object of the turn on delay is to clear all latches and reset all timers.

STAIN PUMP LOGIC

The stain pump logic circuitry is outlined at 521. When a logic 1 is applied to plug P-14, pin 4, it is applied to the disabled bounceless flip-flop 522, pin 522a. When the signal at pin 523 goes to a 1 (transport motion inhibited), the output of 521 pin 524 will go low. This logic 0 is sent to gate 525, and its output goes to a logic 1. This logic 1 output is applied to the clock input of latch 511. The $\overline{Q}$ output of latch 511 goes to a logical 0 and triggers timer 520, the output 520a of which goes to logical 1 for a period determined by the setting of a 200 K stain potentiometer 209 (FIG. 14B) on plug P-14, pin 5. This logic 1 is sent to nor-gate 526, the output of which is used to clear latch 511. The output 520a of timer 520 is also sent to the inverting buffer 527. The output of 527 goes to logic 0 and is sent on conductor 529 to the stain pump motor drive circuitry outlined at 528, FIG. 15D, enabling the stain pump for the period of the logic 0 (typically 1.5 seconds).

BUFFER PUMP LOGIC

The buffer pump logic, shown in block form at 530 in FIG. 15B, is similar to the stain pump timer circuit described above. When a logic 1 is applied to plug P-14, pin 6 in conjunction with a transport stopped signal being at a 1 (plug P-14 applied to a bounceless flip-flop similar to 522 and after similar signal processing the output on line 531, a logic 0 for typically 1.5 seconds, enables the buffer pump motor drive circuitry shown in block form at 532, FIG. 15D).

TRANSPORT MOTOR LOGIC

The transport motor logic, shown in block form at 533 in FIG. 15B, is also similar to the buffer pump timer logic circuit 530. Thus, when a logic 0 at plug P-14, pin 13 is applied to a bounceless flip-flop switch similar to that at 522, similar signal processing ensues operating in conjunction with a disabling timer, the disabling time of which is determined by a potentiometer 211 (FIG. 14B) at plug P-14, pin 1 (typically 30 seconds). When the disabling timer has timed out in conjunction with inverter 534, a logic 0 is applied through line 535 to enable the transport motor drive circuitry shown in block form at 536 in FIG. 15D.

RINSE PUMP AND RINSE CAM LOGIC CIRCUITRY

The rinse pump and rinse cam logic circuitry is outlined at 537 in FIG. 15B with the application of a logic 1 to plug P-14, pin 8 followed by the transport stopped signal going to a 0 at the input of inverter 538, a 1 appears at the Q output 539 of latch 513. When the transport stopped signal goes back to a 1 the Q output 539 of latch 513 is clocked into the Q output 540 of latch 512. This 1 at the Q output 540 of latch 512 is used to clear latch 513 via gate 541. The Q output 540 of 512 is also sent to gate 542 where it is nored with rinse cam stop signal from plug P-14, pin 14, and sent to inverter 543 which again inverts it and presents this logic 1 to norgates 544 and 545. A latch 546 fhaving Q and $\overline{Q}$ outputs 547 and 548 are nanded with the logic 1 from 543 and therefore either the output of 544 or 545 will be at a logic 0.

Figure 15C:
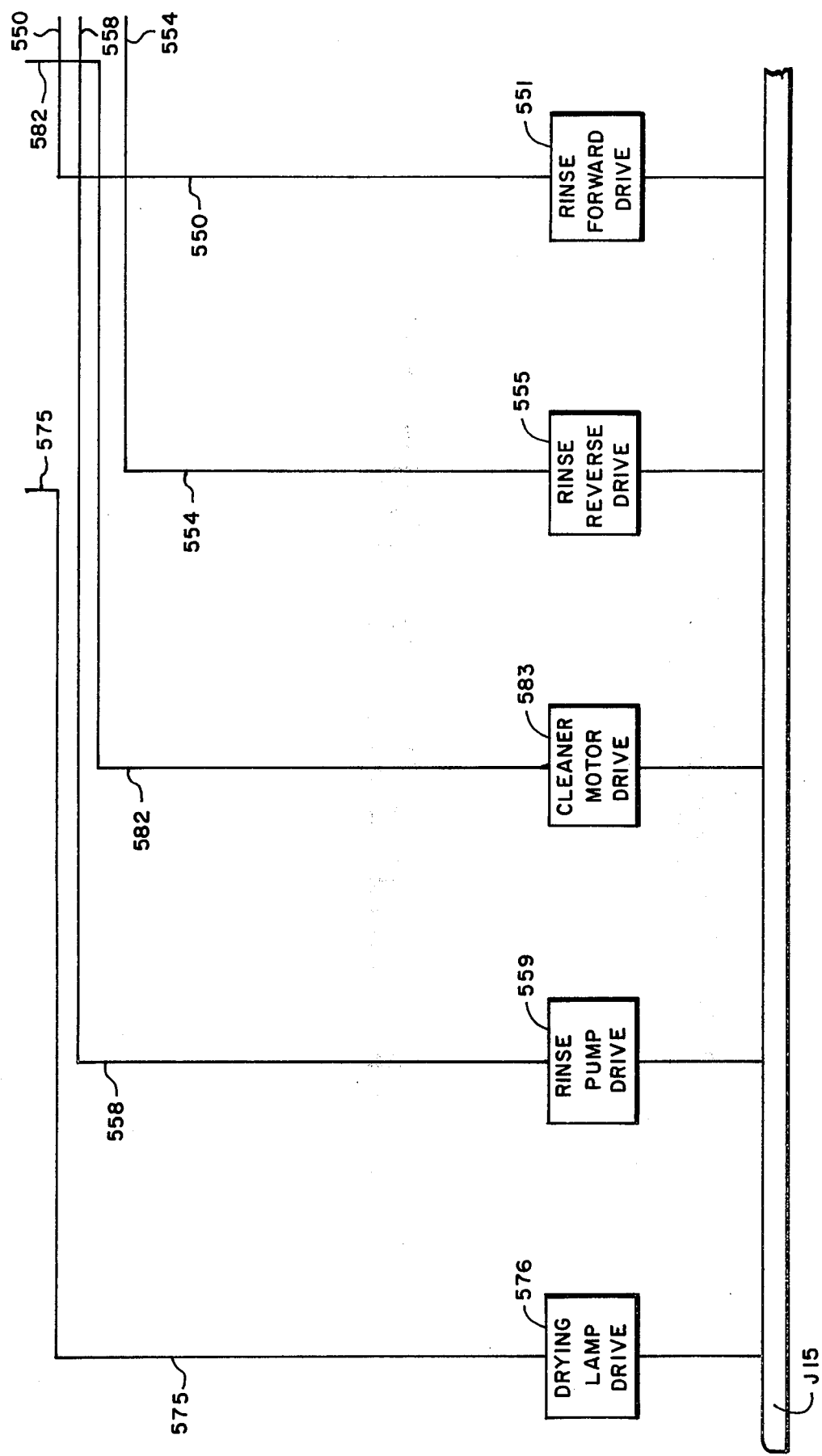

At the start of the rinse cycle plug P-14, pin 14 is at a logic 0 and clears latch 546 at 549. Therefore, 546's $\overline{Q}$ output 548 is at a 1 and the output of 545 is low which enables by way of lead 550, the rinse cam forward motor circuitry 551, shown in block form in FIG. 15C. When the signal at plug P-14, pin 14 goes to a logic 1, latch 512 through gate 552 is cleared while the output of 542 remains low which continues to present a 1 from 543 to both 544 and 545.

Eventually the rinse cam motor actuates the rinse cam reverse switch 307 and plug P-14, pin 9 goes to a logic 0 which is inverted by inverter 553 and clocks a 1 into the Q output 547 of 546. The output of 545 now goes to a 1 disabling rinse-cam forward motor circuitry 551 and the output of 544 goes to a 0. This 0 from 544 enables by way of lead 554 the rinse cam reverse motor circuitry 555 shown in block in FIG. 15C. Plug P-14, pin 9 will then go to a 1 and reverse motor circuitry 555 will remain enabled until the rinse cam stop switch 308 is actuated (returning plug P-14, pin 14 to a 0). The presents a 0 to 544 and 545 whose outputs go high disabling both 555 and 551. During the rinse cycle, the outputs of 544 and 545 are nored by gate 556, inverted by 557 to a 0, thus enabling by way of lead 558 the rinse pump motor drive circuitry 559, shown in block form in FIG. 15C.

WEDGER MOTOR LOGIC CIRCUITRY

The wedger motor logic circuitry is outlined in FIG. 15A at 560 with the application of a 0 at plug P-14, pin 23 and a 1 at plug P-14, pin 21, latch 508 $\overline{Q}$ output 561 is clocked to a 0 by a 1 from bounceless flip-flop 562 as connected by lead 563. The $\overline{Q}$ 561 from 508 is negatively ored with the home switch signal plug P-14, pin 10, via gate 564, by or gate 565 and sent to gate 566 where it is nanded with the slide in position signal via inverter 566a (plug P-14, pin 24 must be 0) and the dry and/or clean signals from gate 567 (plug P-14, pin 7 via gate 516 must be 1 and timer 519 at pin 568=0). When the wedger arm advances, the home switch output at plug P-14, pin 10 goes to a 1 which clears latch 508 via gates 564, 569a and 570b. The output of 564 is also negatively ored with the output of latch 508 at gate 565 which continues the drive command until the home switch output at P-14, pin 10 goes to a 0.

This low composite signal from gate 566 is inverted and buffered by inverter 571 whose output goes to a 1 and enables the D.C. servo via 2 dropping diodes 571a and 571b and the length potentiometer on plug P-14, pin 28 not shown. With a 0 applied to plug P-14, pin 10 (indicating the wedger is in the home position) the output of 564 goes to a 1, clocking a 0 into the $\overline{Q}$ output 572 of latch 510. This 0 triggers timer 519, whose logic 1 output on pin 568 duration is determined by the dry potentiometer on plug P-14, pin 28. The pin 568 signal is sent to inverter 574 where it is inverted and enables through lead 575 the drying lamp drive circuitry shown in block form at 576 in FIG. 15C. As indicated above, the typical lamp operation time is 30 seconds.

In addition, the 1 from 519 pin 568 is inverted by gate 577 which clears latch 510 at 578. Also, when 564's output goes to a 1 it is sent to latch 518 clocking a 0 into the $\overline{Q}$ output 579. This 0 output is sent to gate 580 and inverted. The 1 from 580 is again inverted by inverter 581 and sent by lead 582 which enables the clean cam motor direve circuitry shown in block form at 583 in FIG. 15C.

When the clean motor starts to drive, a 0 is presented to 516 from plug P-14, pin 7 and inverted. This 1 is presented to inverter 517 inverted again and is used to clear latch 518 at 584. Also, when the clean motor starts to drive, a 0 is presented to 580, inverted, sent to 581, inverted again and continues to be sent to the clean cam motor drive circuity 583 until the signal at plug P-14, pin 7 goes to a 1.

OUTPUT MAGAZINE AND RINSE LEVEL LOGIC (ALARM LOGIC) SYSTEM

The output magazine and rinse logic system is represented by outline 585 in FIG. 15A. When a logic 0 is applied to plug P-14, pin 26, output magazine switch, and/or a logic 1 is applied to plug P-14, pin 25, rinse level switch, the output of a gate 586 output goes to a 1, at 587 clocking a 0 into the $\overline{Q}$ output 588 of latch 509. This 0 is negatively anded, with transport run 589 by gate 590. This enables timer 591 when gate 590 output is 0. Timer 591 is used in a gated oscillator mode. The square wave output of 591 ($\cong$ 1 KHZ) drives the base of transistor 592 whose collector is externally tied through plug P-14, pin 17 to 5 volts through a 4 ohm speaker 340 (FIG. 4) in series with resistor 539 on P-14, pin $\overline{f}$ on the FIG. 15B thus giving an audible tone.

A 12V lamp on P-14, pin $\overline{j}$ is also driven by a transistor 594. An inverter 595 presents a 0 to the base of transistor 594 turning it on when gate 586 goes to a 1. The audible tone can be disabled by applying a 0 to P-14, pin $\overline{h}$ which clears latch 509 thus disabling timer 591.

A.C. MOTOR AND LAMP DRIVE CIRCUITRY

For simplification, all the A.C. drive circuits are identical with the exception of one small variation in the wedge drying lamp circuit which will be described below. Thus, the illustration of description of the stain pump drive circuit 528 (FIG. 15D) will serve to describe all such circuits and the slight difference found in circuit 576 is discussed below. These circuits include the transporter circuit 536, buffer pump circuit 532, rinse station cam forward circuit 551 and cam reverse 555, cleaner cam motor circuit 583, rinse pump motor circuit 559 and smear drying lamp circuit 576.

In circuit 528 a 0 placed via lead 529 at the input of an optically controlled SCR unit 596 of the type MCS-2 turns on a conventional LED, inside the optically controlled SCR 596 (not shown), which in turn will turn on the SCR inside (not shown) if voltage is present across the resistor 597 at pin 598 of the optically controlled SCR unit 596. A diode bridge 599 is used to rectify the voltage across the SCR in the optically controlled SCR unit 596. A transistor, resistor network is included to provide a soft fire circuit which prevents firing above 6 volts line voltage to eliminate radio frequency interference. Thus, at approximately 6 volts the transistor 600 connected as illustrated operates as a 6 volt Zener diode, turning on transistor 601 connected across resistor 597 when the voltage exceeds 6 volts line, thus shorting out the gate to cathode not shown of the optically controlled SCR unit 596. When the optically controlled SCR unit 596 fires between −6 and +6V line, a triac 602 which may be a SC-136B triac turns on and remains on until the input 595 to the optically controlled SCR unit 596 goes to 1 and the current through the triac 602 goes through 0 amps.

The lamp drying circuit 576 is identical to the circuits described above with the exception that the triac, see 576a, FIG. 14B, is located on an external heat sink.

D.C. WEDGER MOTOR SERVO CIRCUITRY

Figure 15D:
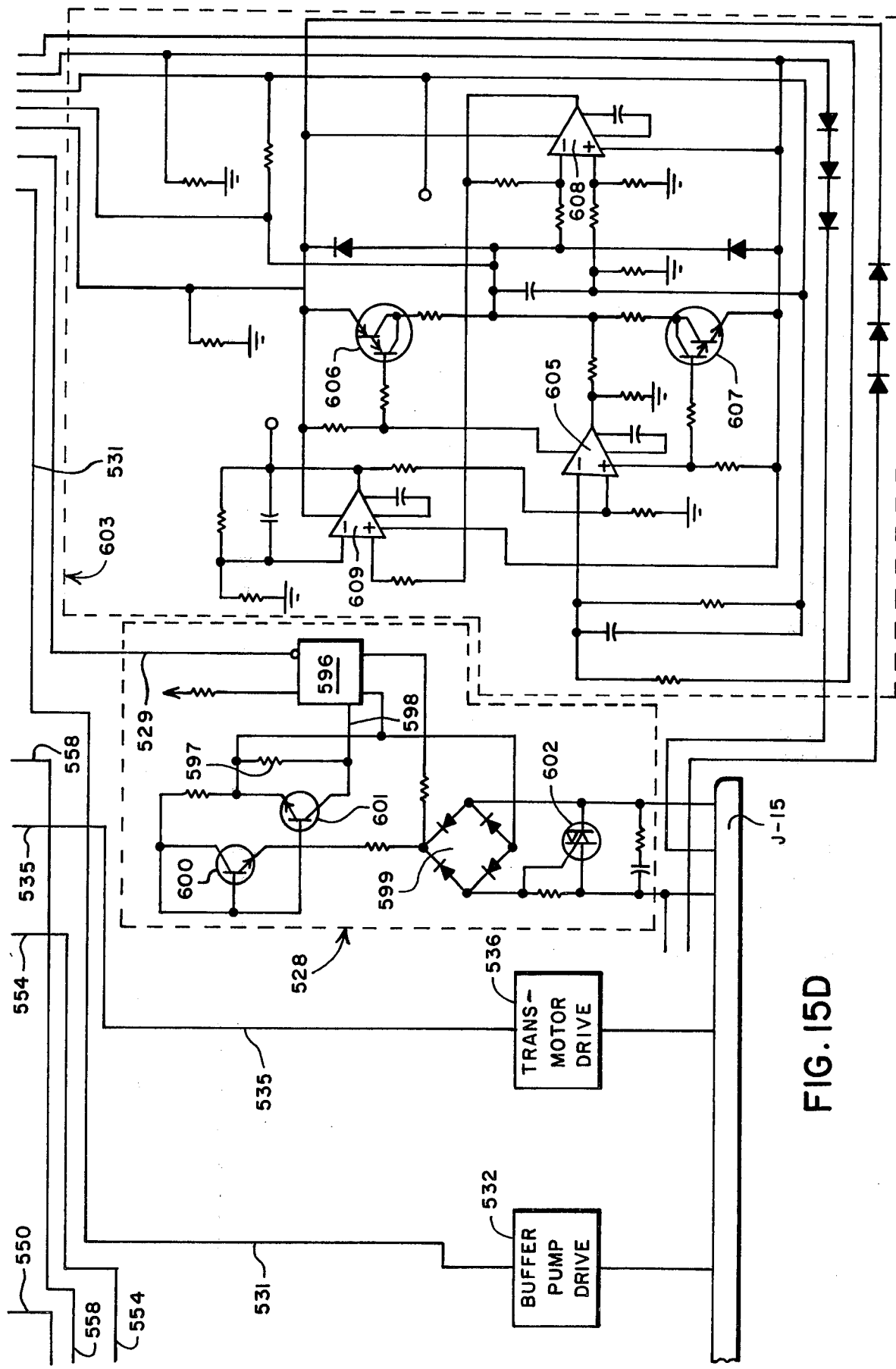

The D.C. motor control circuitry is denoted by 603 on FIG. 15d and is adapted to provide precise speed and start-stop control to the smear making apparatus of the invention. Thus, the smearing apparatus by means of a servo system is designed to provide motor acceleration to a selected stable RPM without a settling time of 100 msec. Deceleration from the set RPM to a complete halt occurs within the same time interval.

Functionally, the drive command from the logic at plug P-14, pin 30 generates a servo loop imbalance proportional to the setting of a length potentiometer (not shown) which is approximately +0.8V to +2.8V which in turn causes drive current to flow through the wedger motor 67 (FIG. 6) until it reaches a rotational velocity such that the back EMF of the motor is sufficient to correct the imbalance. When turned off, the servo delivers sufficient reverse current to bring the motor quickly to a halt.

The servo system can be divided into three basic modules. First, a resistor 604 (FIG. 15A) provides a stable D.C. reference voltage for speed control. An amplifier 605 in conjunction with transistors 606 and 607 acts as a high gain current amplifier with current feedback. An amplifier 608 serves to extract the back EMF of the wedger motor, which is amplified by amplifier 609 to provide velocity feedback to amplifier 605. Thus designed, the closed loop response of the servo system provides a dynamic transfer characteristic, i.e. drive signal to shaft rotation, of about 14 Hz.

Under normal loading conditions, the servo will provide an angular velocity at the wheel 69 (FIG. 4) of from 9 to 30 RPM. Corresponding to 0.8V to 2.8V at Pin 30 of plug P-14. At 30 RPM the motor will demand about −200 ma with a voltage drop of about −10 vdc and −150 ma at −4.2V for 9 RPM. Starting and stopping torque will demand about −900 ma starting and +1.25 ma stopping current from the servo.

The embodiments of the invention is which an exclusive property or right is claimed are defined as follows:

1. An integral smeared microscope slide preparation station comprising in combination:
    smearing means for automatically establishing a smear of a fluid sample placed on a microscope slide, said smearing means further comprising;
    slide support means,
    spreading member having a smearing edge thereon for producing said smear,
    means for maintaining said smearing edge in parallel relation to the surface of said slide during the smearing operation,
    means for controlling the contact pressure between said smearing edge and said slide,
    staining means for automatically staining smeared slides, said staining means further comprising;
    conveyer means for carrying slides in a substantially horizontal disposition during the staining operation performed thereon,
    a plurality of liquid dispensing means disposed along said conveyer means for applying a plurality of liquids to the upper surface of slides on said conveyer means at sequential, pre-determined intervals,
    control means for controlling the operation of said smearing means and said staining means.

2. The apparatus of claim 1 wherein said smearing means further comprises slide dispensing means for dispensing slides in position for smearing.

3. The apparatus of claim 2 wherein said slide dispensing means further comprises a reloadable storage magazine for storing a plurality of slides to be dispensed, and feeding means for feeding slides singly from said storage means to the smearing position on said slide support means.

4. The apparatus of claim 1 wherein said slide support means further comprises positioning means for retaining slides in a substantially horizontally disposed fixed relation to said smearing member during said smearing operation.

5. The apparatus of claim 1 wherein said smearing means further comprises:
    a vertically, pivotally mounted reciprocating smearing arm means;
    a self-leveling head means journal mounted at the forward end of said arm means, said head means carrying said spreading member in fixed relation thereto such that the smearing edge thereof is disposed in parallel relation to the top of a horizontally disposed slide in the smearing position, and the spreading member itself is disposed at a substantially fixed angle with said slide when in contact therewith;
    the means for controlling the contact pressure between said smearing edge and said slide comprising adjustable counterweight means mounted on the rearward end of said smearing arm means; and
    drive means for imparting reciprocal motion to said smearing arm means.

6. The apparatus of claim 1 wherein said smearing means further comprises cleaning in synchronized conjunction with the said spreading means by said control means, and cleaning means including resilient wiping means for cleaning said spreading member after each said smearing operation.

7. The apparatus of claim 1 wherein said smearing means further comprises smear drying means for drying said smears after each smearing operation.

8. The apparatus of claim 1 wherein said control means further comprises:
    slide sensing means for sensing the presence of a slide in the smearing position;
    actuating means for activating a drive means for reciprocally driving said spreading member through a smearing cycle in which said spreading member is moved forward to engage a liquid sample placed at a pre-determined location on said slide and then moved in reverse to make said smear;
    stopping means for abruptly stopping said smearing drive means such that said spreading member is at a pre-determined, rearward position after said smearing cycle.

9. The apparatus of claim 8 wherein said control means further comprises adjustable speed control means for controlling the speed of movement of said spreading member.

10. The apparatus of claim 9 wherein said control means further comprises:

actuating means to activate cleaning means for cleaning said spreading member when said spreading member reaches said rearward position at the end of said smearing cycle;

actuating means to activate drying means to dry said slide after said smearing cycle; and adjustable timing means for controlling the time of operation of said drying means.

11. The apparatus of claim 1 wherein said conveyer means includes:

input conveyor means for sequentially accepting, storing and advancing a plurality of ordered, smeared slides prior to the staining thereof;

staining conveyor means for sequentially accepting a plurality of said slides from said input conveyer means and sequentially advancing same in a substantially flat, level position;

output conveyer means for sequentially accepting from said staining conveyer means a plurality of said slides after the staining thereof, said output conveyer having a storage magazine means for sequentially storing said slides after said staining operation;

drive means for intermittently advancing said staining conveyer means in an indexing manner one slide position at each of a plurality of successive pre-determined timed intervals;

synchronization means for synchronizaing the advancement of said input and said output conveyer means with the advancement of said staining conveyer means such that said input and said output conveyer means also index the corresponding amount of one slide position with each intermittent advancement of said staining conveyer means; and transfer means for sequentially transferring each of said plurality of slides from said input conveyer means to said staining conveyer means and from said staining conveyer means to said output conveyer means.

12. The apparatus of claim 11 including control means associated with said drive means, said control means including adjustable timing means for controlling said interval between the indexing of said drive means.

13. The apparatus of claim 12 wherein said control means further comprises manual override means enabling said staining conveyer drive means in spite of said timing means.

14. The apparatus of claim 1 wherein said liquid dispensing means further comprises a plurality of liquid dispensing stations, each of said liquid dispensing stations including:

sensing means for sensing the presence of a slide in a substantially horizontal pre-determined positional relationship to said liquid dispensing station;

pump means for propelling said liquid, said pump means being synchronized with said sensing means;

means for applying liquid on the upper surface of said sensed slide; and adjustable control means for said pump means, said control means causing said pump means to apply a pre-determined amount of liquid on said slide in response to said sensing means indicating the presence of a slide in position to receive said liquid.

15. The apparatus of claim 14 wherein each of said liquid dispensing stations further includes:

reservoir means for storing liquid to be dispensed; and wherein said means for applying said liquid is a resilient hollow tubing means which conveys said liquid from said reservoir means to said slide; and support means for supporting said tubing means such that said liquid is dispensed at a pre-determined angle and distance with respect to the surface of said slide.

16. The apparatus of claim 14 wherein said adjustable control means for controlling the amount of liquid dispensed by said pump means includes enabling means and adjustable timing means for determining the period of operation of said pump means.

17. The apparatus of claim 16 wherein said control means further comprises override means enabling manual operation of said pump means in spite of said sensing means for priming and calibration of said pump means.

18. The apparatus of claim 14 wherein said plurality of liquid dispensing stations include:

a first liquid dispensing station of applying a pre-determined amount of stain on the upper surface of a slide sensed by said sensing means to be in position at said first liquid dispensing station;

a second liquid dispensing station beyond said first dispensing station for applying an amount of a buffer solution on said stained slide sensed in position at said second liquid dispensing station at a pre-determined interval after said application of said stain;

a third liquid dispensing station beyond said second dispensing station for applying an amount of a rinse solution to rinse said stained slide at a pre-determined interval after application of said buffer solution.

19. The apparatus of claim 18 further comprising mixing means positioned in close relation to said buffer dispensing means, said mixing means directing an amount of air toward said slide at a pre-determined attitude of mixing said stain and said buffer to assure proper reaction therebetween.

20. The apparatus of claim 18 including tilting means for tilting and maintaining said slide at an acute angle on one edge thereof during the rinsing of said slide.

21. The apparatus of claim 18 wherein said third liquid dispensing station further comprises traversing rinsing mechanism for applying said rinse solution along the entire length of said slide.

22. The apparatus of claim 18 further comprising drying means beyond said third liquid dispensing station for directing an amount of drying air across said slide after completion of the rinsing thereof, and air delivery means for providing an amount of air for said drying means.

23. The apparatus of claim 22 further comprising heating means for heating said air for said drying means.

24. The apparatus of claim 1 further comprising motor-driven rotary mixing means for mixing sealed containers of said liquid samples prior to applying a portion thereof on a slide in position for smearing, said mixing means provided with a rotatable member having a plurality of recesses suitably shaped to receive said containers and supported at an attitude which allows said containers to be retained therein by gravity.

* * * * *

UNITED STATES PATENT OFFICE
CERTIFICATE OF CORRECTION

PATENT NO. : 4,034,700
DATED : July 12, 1977
INVENTOR(S) : William W. Bassett, et al.

It is certified that error appears in the above—identified patent and that said Letters Patent are hereby corrected as shown below:

In claim 6, column 22, line 40, after "cleaning", insert --means operated-- and at line 42, after "means", delete "and" and insert --said--.

In claim 18, column 23, line 22, after "station", delete "of" and insert --for--.

Signed and Sealed this

Twenty-fifth Day of October 1977

[SEAL]

Attest:

RUTH C. MASON
Attesting Officer

LUTRELLE F. PARKER
Acting Commissioner of Patents and Trademarks